US011189855B1

(12) United States Patent
O'Neill et al.

(10) Patent No.: US 11,189,855 B1
(45) Date of Patent: Nov. 30, 2021

(54) REDOX MEDIATORS AS ELECTROLYTE ADDITIVES FOR ALKALINE BATTERY CELLS

(71) Applicant: Apple Inc., Cupertino, CA (US)

(72) Inventors: Cory R. O'Neill, Cupertino, CA (US); Steven Kaye, Oakland, CA (US)

(*) Notice: Subject to any disclaimer, the term of this patent is extended or adjusted under 35 U.S.C. 154(b) by 35 days.

(21) Appl. No.: 16/855,170

(22) Filed: Apr. 22, 2020

(51) Int. Cl.
| | |
|---|---|
| *H01M 8/18* | (2006.01) |
| *H01M 50/46* | (2021.01) |
| *H01M 8/083* | (2016.01) |
| *C07D 213/22* | (2006.01) |

(52) U.S. Cl.
CPC .......... *H01M 8/188* (2013.01); *C07D 213/22* (2013.01); *H01M 8/083* (2013.01); *H01M 50/46* (2021.01)

(58) Field of Classification Search
CPC .................................................. H01M 8/188
See application file for complete search history.

(56) References Cited

U.S. PATENT DOCUMENTS

| | | | |
|---|---|---|---|
| 5,162,169 A | 11/1992 | Tomantschger et al. | |
| 5,837,158 A | 11/1998 | Shepodd et al. | |
| 8,153,410 B2 | 4/2012 | Jaffe | |
| 8,163,410 B2 | 4/2012 | Fulop et al. | |
| 2001/0038939 A1 | 11/2001 | Bailey | |
| 2008/0187824 A1 | 8/2008 | Tomantschger | |
| 2009/0068531 A1 | 3/2009 | Sawa et al. | |
| 2011/0014532 A1* | 1/2011 | Knuckey | H01M 4/9008 429/416 |
| 2012/0189896 A1 | 7/2012 | Zhou et al. | |
| 2012/0263995 A1 | 10/2012 | Naito et al. | |
| 2014/0127542 A1 | 5/2014 | Li et al. | |
| 2014/0154542 A1 | 6/2014 | Issaev et al. | |
| 2014/0178735 A1* | 6/2014 | Wang | H01M 8/20 429/105 |
| 2015/0200393 A1 | 7/2015 | Li et al. | |
| 2015/0236543 A1* | 8/2015 | Brushett | H01M 8/188 429/81 |

(Continued)

FOREIGN PATENT DOCUMENTS

| | | |
|---|---|---|
| EP | 1125336 A1 | 8/2001 |
| EP | 3435473 A1 | 1/2019 |

(Continued)

OTHER PUBLICATIONS

U.S. Appl. No. 16/245,542, "Non-Final Office Action", dated May 11, 2021, 14 pages.
U.S. Appl. No. 16/748,586, "Non-Final Office Action", dated May 14, 2021, 12 pages.
U.S. Appl. No. 16/538,660, "Non-Final Office Action", dated Feb. 16, 2021, 12 pages.

(Continued)

*Primary Examiner* — Brian R Ohara
(74) *Attorney, Agent, or Firm* — Kilpatrick Townsend & Stockton, LLP

(57) ABSTRACT

A redox mediator-containing electrolyte incorporated into a battery cell is described. The redox mediator-containing electrolyte includes water, at least one hydroxide salt dissolved in the water, and at least one redox mediator incorporated into the water. The at least one redox mediator increases at least one of a rate capability or a cycle life of the battery cell by at least 10%. Also described are battery cells that may include a positive electrode, a negative electrode, and the redox mediator-containing electrolyte. The battery cells may further include an ion-selective material that diffuses hydroxide ions through the material at a faster rate than at least one of the redox mediators.

27 Claims, 7 Drawing Sheets

(56) References Cited

U.S. PATENT DOCUMENTS

| | | | |
|---|---|---|---|
| 2015/0280259 A1* | 10/2015 | Anderson | H01M 8/188 429/409 |
| 2016/0049679 A1 | 2/2016 | Stevens et al. | |
| 2016/0248113 A1 | 8/2016 | He et al. | |
| 2017/0133689 A1 | 5/2017 | Moore et al. | |
| 2017/0250434 A1* | 8/2017 | Gennett | H01M 8/188 |
| 2018/0079721 A1* | 3/2018 | Armand | H01M 8/1016 |
| 2018/0097248 A1* | 4/2018 | Nariyama | H01M 4/86 |
| 2018/0175427 A1* | 6/2018 | Nariyama | H01M 8/225 |
| 2018/0175470 A1* | 6/2018 | Bai | H01M 4/382 |
| 2018/0294454 A1 | 10/2018 | Mackenzie et al. | |
| 2018/0316063 A1 | 11/2018 | Masel et al. | |
| 2019/0036147 A1 | 1/2019 | Yuan et al. | |
| 2020/0212440 A1 | 7/2020 | Kolhekar et al. | |
| 2021/0028457 A1* | 1/2021 | Newhouse | H01M 4/248 |

FOREIGN PATENT DOCUMENTS

| | | | | |
|---|---|---|---|---|
| JP | 0562683 | A | 3/1993 | |
| JP | 3522303 | B2 | 4/2004 | |
| JP | 2009224097 | A | 10/2009 | |
| JP | 2014029818 | A | 2/2014 | |
| WO | 2010111087 | A1 | 9/2010 | |
| WO | 2018213601 | A2 | 11/2018 | |
| WO | 2019023010 | A1 | 1/2019 | |
| WO | WO-2019245461 | A * | 12/2019 | H01M 8/188 |

OTHER PUBLICATIONS

PCT/US2020/060348, "International Search Report and Written Opinion", dated Mar. 12, 2021, 9 pages.
PCT/US2020/060350, "International Search Report and Written Opinion", dated Mar. 12, 2021, 12 pages.
Weng, et al., "Three-Electrolyte Electrochemical Energy Storage Systems Using Both Anion- and Cation-Exchange Membranes as Separators", Energy, vol. 167, Jan. 15, 2019, pp. 1011-1018.
PCT/US2018/033218, "International Preliminary Report on Patentability", dated Nov. 28, 2019, 9 pages.
PCT/US2018/033218, "International Search Report and Written Opinion", dated Nov. 16, 2018, 13 pages.
PCT/US2018/042598, "International Preliminary Report on Patentability", dated Feb. 6, 2020, 10 pages.
PCT/US2018/042598, "International Search Report and Written Opinion", dated Oct. 2, 2018, 14 pages.
U.S. Appl. No. 16/683,091, "Non-Final Office Action", dated Aug. 18, 2021, 22 pages.
Boeva, et al., "Soluble and Highly Ionically Conducting Interpolyelectrolyte Complexes Prepared Via Chemical Template Polymerization of Aniline in the Presence of Perfluorinated Polysulfonic Acid", The Royal Society of Chemistry; vol. 4, 2014, p. 56677-56681.
Thuc, "Study on Synthesis and Characterization of Anion Exchange Membrane Based on Poly (Vinyl Alcohol) Modified by Freeradical Polymerization", International Journal of Electrochemical Science; vol. 15, 2020, pp. 8190-8199.

* cited by examiner

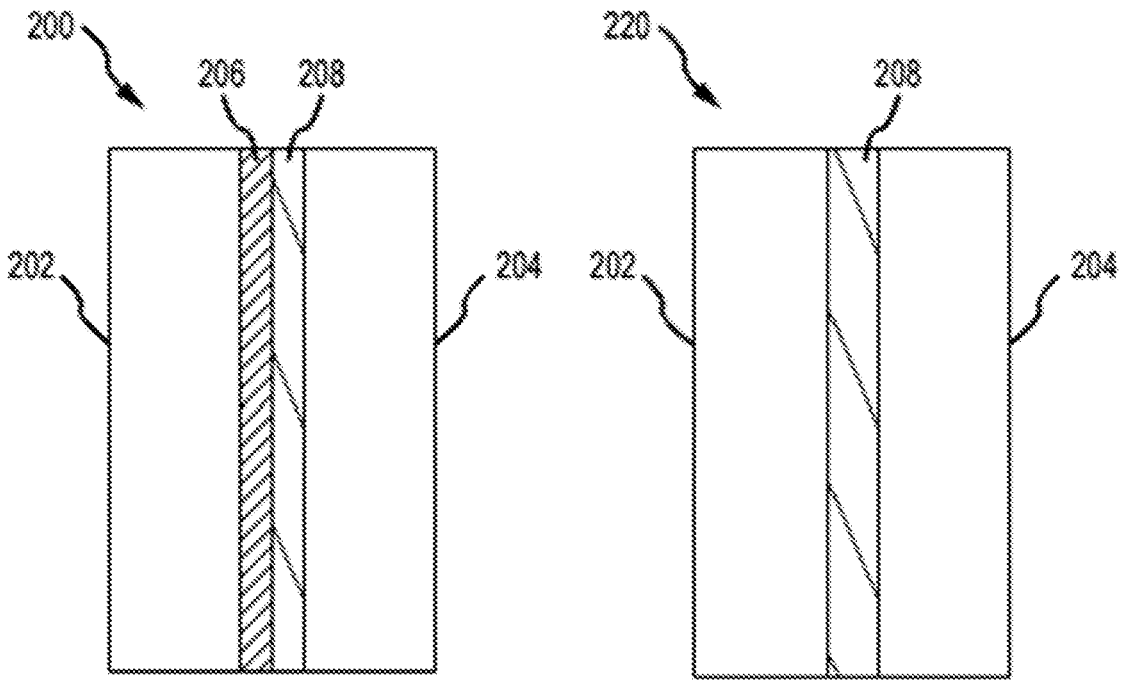
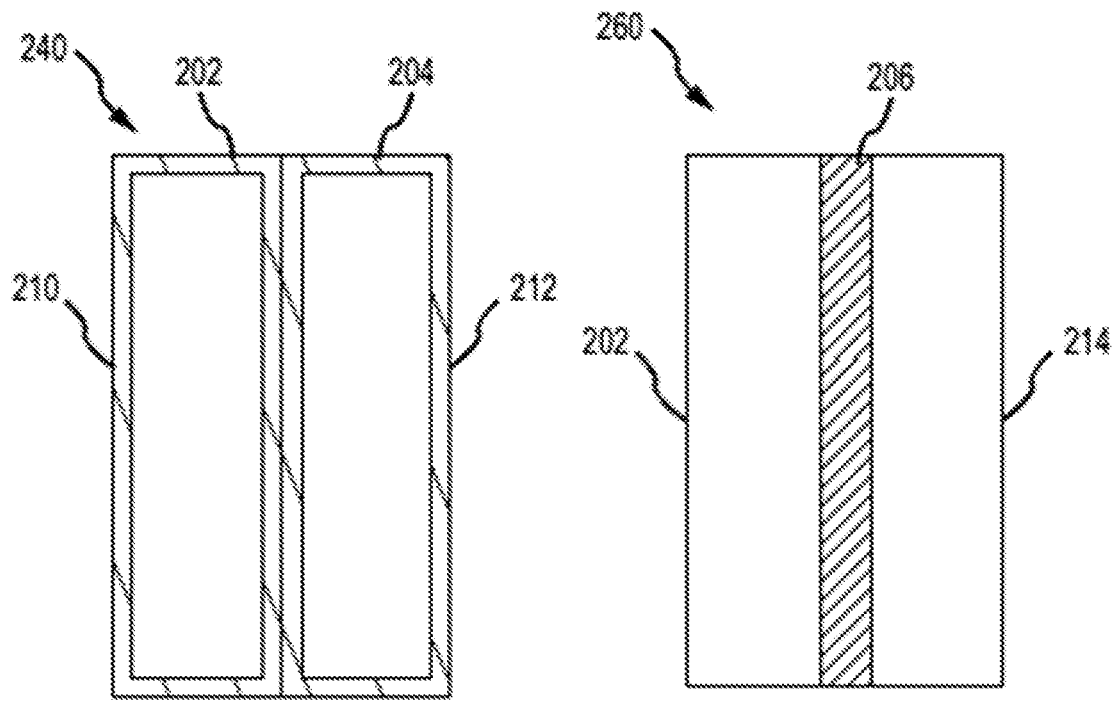

REDOX MEDIATORS AS ELECTROLYTE ADDITIVES FOR ALKALINE BATTERY CELLS

TECHNICAL FIELD

The present technology relates to batteries and battery components and materials. More specifically, the present technology relates to redox mediators as electrolyte additives incorporated into the electrolytes of rechargeable alkaline battery cells.

BACKGROUND

Non-rechargeable ("primary") alkaline-manganese dioxide batteries are one of the most popular type of batteries in the world with worldwide sales currently in the tens of billions of US dollars. They are widely used to power a variety of electronics devices including radios, remote controls, watches, portable lights (e.g., flashlights), and clocks, among many other types of devices. The alkaline-manganese dioxide battery remains popular because of its low cost and ease of manufacture, use of low-toxicity materials, and long shelf-life, among other advantages. The battery's use of safe, low-cost materials and ease of manufacture have encouraged efforts to develop a commercially competitive rechargeable ("secondary") alkaline-manganese dioxide batteries for portable electronics, as well as batteries for larger energy storage and backup needs. Unfortunately, these efforts have encountered a number of significant challenges. Among them are the tendency of the battery's initial charge capacity to rapidly decline after a relatively short number of charging cycles. While there have been attempts to overcome the short cycle lifetimes of secondary alkaline batteries, including the avoidance of deep discharging that increases the formation of electrochemically inactive materials and new formulations of active materials for the electrodes, none so far have led to the development of an economically competitive secondary alkaline-manganese dioxide battery.

BRIEF DESCRIPTION OF THE DRAWINGS

A further understanding of the nature and advantages of the disclosed embodiments may be realized by reference to the remaining portions of the specification and the drawings.

FIGS. 2A-D show simplified schematics of the incorporation of ion-selective material in a battery cell according to the present technology.

Figure 1:
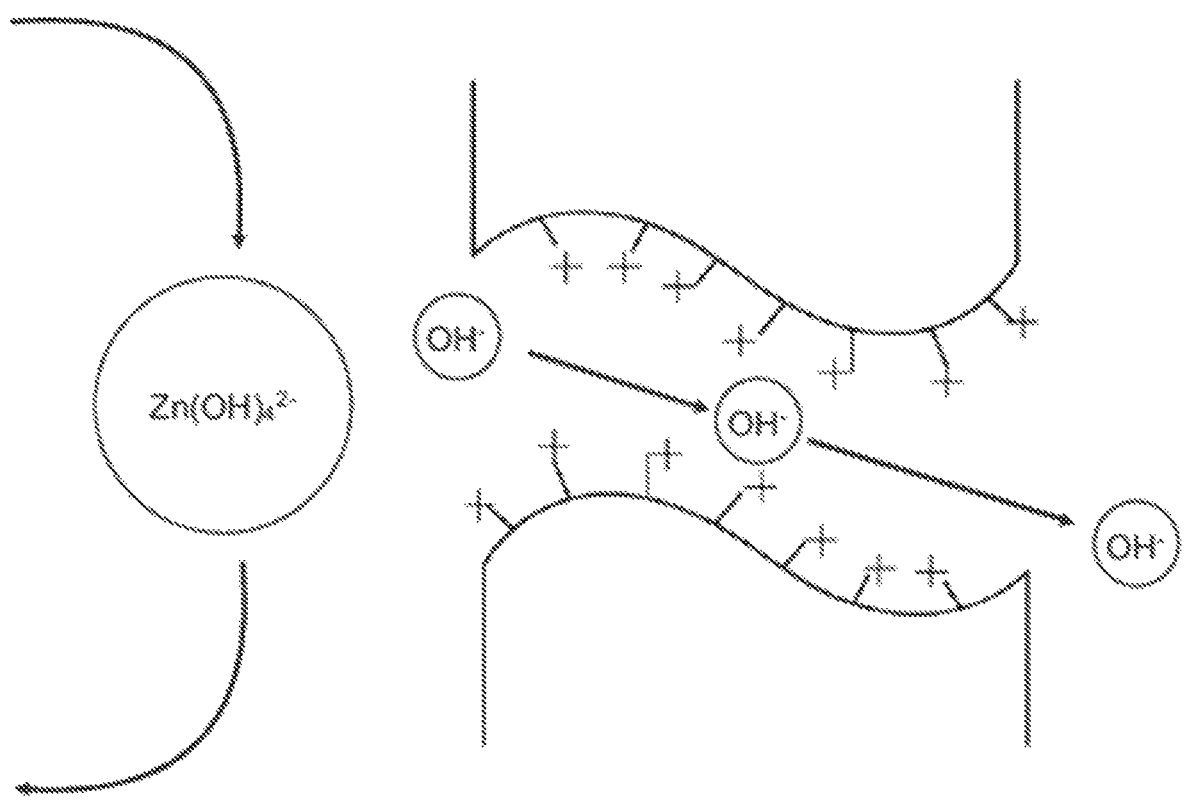
FIG. 1 shows a simplified schematic of an ion-selective barrier according to the present technology.

Several of the figures are included as schematics. It is to be understood that the figures are for illustrative purposes, and are not to be considered of scale unless specifically stated to be of scale. Additionally, as schematics, the figures are provided to aid comprehension and may not include all aspects or information compared to realistic representations, and may include exaggerated material for illustrative purposes.

In the figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

In the present technology, it has been discovered that electrolyte formulations that include one or more redox mediators can improve a number of functional characteristics of a battery cell. Exemplary redox mediators can reduce the activation barrier to redox reactions between reduced and oxidized forms of electrode active materials. They can reversibly oxidize or reduce the electrode active materials at a voltage between an equilibrium voltage of the electrode and the electrode's voltage under load. These functional characteristics include increased rate capability and significantly increased cycle lifetime for the battery, among other characteristics.

The redox mediators incorporated into the electrolyte may include inorganic compounds, organic compounds, or both. In some instances a redox mediator can improve the battery cell's performance at one electrode (e.g., the positive or negative electrode) while having an antagonistic interaction with the counter electrode. Thus, in some embodiments the battery cell may include ion separation material that localizes the redox mediator to specific areas of the battery cell where it has beneficial effects. For example, a positive-electrode redox mediator may be localized to interact with only the positive electrode and may be isolated from the negative electrode. Similarly, a negative-electrode redox mediator may be localized to interact with only the negative electrode and may be isolated from the positive electrode. In additional instances, the redox mediator improves performance at both the positive and negative electrodes of the battery, and no materials are required to localize the redox mediator at only one electrode.

In many embodiments, the redox mediators are incorporated into a highly-alkaline, aqueous electrolyte solution or gel. Exemplary electrolytes may include water, a hydroxide salt, and the redox mediator (among other electrolyte additives), and they may have a pH of 14 or more. As the battery cell progresses through charging and discharging cycles, the electrolyte will also include electrode species (i.e., molecules and ions) that have migrated into the electrolyte. These may include manganese-containing species from the positive electrode such as manganese ions. If zinc is present in the negative electrode, the electrolyte may include zinc-containing species such as zincate ions (i.e., $Zn(OH_4)_{2-}$). The redox mediators are selected to be stable at the pH of the electrolyte, and also to be stable at the operating voltages of the electrodes during charge and discharge cycles. If the redox mediator is localized to one electrode, it may be selected to be stable at the operating voltages of that electrode.

Specific embodiments include redox mediator-containing electrolytes that are incorporated into a battery cell. The redox mediator-containing electrolytes may include water, a least one hydroxide salt dissolved in the water, and at least one redox mediator. The at least one redox mediator may include at least one of an inorganic compound and an organic compound. For example, the redox mediator-containing electrolyte may include a single redox mediator or it may include two or more redox mediators. Additional examples include a redox mediator-containing electrolyte that includes a single redox mediator, two redox mediators, three redox mediators, four redox mediators, etc.

The redox mediators can increase a performance characteristic of the battery cell by at least 10%. For example, the presence of one or more redox mediators in the electrolyte can increase rate capability and/or the cycle life of the battery cell by at least 10%, when compared to an otherwise identical battery cell that lacks the one or more redox mediators. For redox mediators that enhance a battery cell's rate capability, a battery cell with a rate capability of, for example, 100 mAh/g at 0.5C without the one more redox mediators would increase its rate capability to at least 110 mAh/g at the same C-rating (i.e., 0.5C) when the one or more redox mediators are present in the battery cell's electrolyte. For redox mediators that enhance a battery cell's cycle life, a battery cell with a cycle life of, for example, 100 charge/discharge cycles before declining to 80% its maximum reduction capacity without the one more redox mediators would increase its cycle life to at least 110 cycles before declining to the same 80% level when the one or more redox mediators are present in the battery cell's electrolyte.

Specific embodiments also include a battery cell that includes a positive electrode, a negative electrode, and an redox mediator-containing electrolyte. The redox mediator-containing electrolyte may include water, at least one hydroxide salt dissolved in the water, and at least one redox mediator incorporated into the water. The at least one redox mediator may include at least one of an inorganic compound and an organic compound. The presence of the at least one redox mediator increases at least one of (i) a rate capability or (ii) a cycle life of the battery cell by at least 10%. Additional details about the redox mediator-containing electrolytes and the battery cells in which they may be incorporated are provided below.

Exemplary Redox Mediator-Containing Electrolytes

Exemplary redox mediator-containing electrolytes include water and at least one hydroxide salt dissolved in the water to create an alkaline electrolyte. Examples of hydroxide salts include alkali metal hydroxide salts such as lithium hydroxide (LiOH), sodium hydroxide (NaOH) and potassium hydroxide (KOH), among other alkali metal hydroxides. Examples further include alkaline earth metal hydroxide salts such as magnesium hydroxide ($Mg(OH)_2$), calcium hydroxide ($Ca(OH)_2$), strontium hydroxide ($Sr(OH)_2$), and barium hydroxide ($Ba(OH)_2$), among other alkaline earth metal hydroxides. Examples still further include ammonium hydroxide salts such as ammonium hydroxide and tetramethylammonium hydroxide, among others. Also contemplated are combinations of two or more hydroxide salts such as LiOH+KOH; NaOH+KOH; LiGH+NaOH; and LiGH+NaOH+KOH; among other examples.

Exemplary concentration ranges of the hydroxide salts (e.g., KOH) include about 10 wt. % to about 80 wt. % based on the total weight of the electrolyte solution. Additional exemplary concentration ranges for the hydroxide salts include about 20 wt % to about 70 wt. %; about 30 wt. % to about 60 wt. %; and about 35 wt. % to about 55 wt. %, among other exemplary concentration ranges. In terms of molar concentrations of hydroxide ion ($OH^-$), the hydroxide salts may produce [$OH^-$] molar concentrations ranging from about 4M to about 15M, for example a range of about 9M to about 12M. Examples of specific [$OH^-$] molar concentrations include about 6M, about 9M, about 12M, and about 15M, among other [$OH^-$] molar concentrations. These concentration ranges for the hydroxide salts produce alkaline electrolytes with exemplary room temperature pHs of greater than 9, greater than 10, greater than 11, greater than 12, greater than 13, greater than 14, etc. Exemplary pH ranges also include about 12 to about 18, about 13 to about 18, about 14 to about 18, about 14 to about 17, about 14 to about 16, and about 14 to about 15, among other pH ranges.

The redox mediator-containing electrolytes include electrolytes having exemplary OH-ion conductivity ranges of 1 mS/cm to 900 mS/cm. Additional exemplary OH– ion conductivity ranges include 10 mS/cm to 800 mS/cm, 25 mS/cm to 700 mS/cm, 50 mS/cm to 600 mS/cm, among other conductivity ranges. The redox mediator-containing electrolytes include electrolytes having exemplary viscosity ranges of 0.1 cP to 10 cP. Additional exemplary viscosity ranges include 0.2 cP to 8 cP, 0.3 cP to 6 cP, 0.4 cP to 4 cP, and 0.5 cP to 3 cP, among other viscosity ranges.

Additional exemplary redox mediator-containing electrolytes include alkali metal hydroxide-containing solids (e.g., dry powders and slurries of particles in a liquid medium) and gels. The electrolyte solution, gel, or solid (e.g., slurry) may be incorporated into the electrode active materials (e.g., the positive active materials and the negative active materials) before they are formed into electrodes. The electrolyte solution, gel, or solid may be incorporated into an ion-selective material. The electrolyte solution, gel, or solid may be absorbed into or coated onto one or more components of the battery cell including the positive electrode, the negative electrode, and/or a separator if one is present in the battery cell.

Exemplary redox mediator-containing electrolytes include at least one redox mediator. These redox mediators may be incorporated into the electrolyte by dissolving them into the water or aqueous alkaline solution, or mixing them with the water or aqueous alkaline solution if they are not completely soluble. Depending on the redox mediator, they may be combined with the water or aqueous alkaline solution as a dry solid, a liquid, a mixture in a carrier (e.g., water), a suspension in carrier, a slurry, or an emulsion, among other forms.

The at least one redox mediator may be incorporated into the electrolyte at a concentration that ranges, for example, from 0.01 wt. % to 50 wt. % of the final electrolyte. Additional exemplary ranges can include on the lower end about 0.01 wt. %, about 0.05 wt. %, about 0.1 wt. %, about 0.5 wt. %, about 1 wt. %, about 2 wt. %, about 3 wt. %, about 4 wt. % about 5 wt. %, about 6 wt. %, about 7 wt. %, about 8 wt. %, about 9 wt. %, about 10 wt. %, about 15 wt. %, about 20 wt. %, about 25 wt. %, about 30 wt. %, and about 40 wt. %, among other values. Additional exemplary ranges can include on the upper end about 50 wt. %, about 40 wt. %, about 30 wt. %, about 25 wt. % about 20 wt. %, about 15 wt. % about 10 wt. %, about 9 wt. %, about 8 wt. %, about 7 wt. %, about 6 wt. %, about 5 wt. %, about 4 wt. %, about 3 wt. %, about 2 wt. %, about 1 wt. %, about 0.5 wt. %, about 0.1 wt. %, among other values.

The at least one redox mediator may have an oxidation/reduction potential that is between the thermodynamic potential for the battery active materials and the end voltage of the electrode on charge/discharge. Exemplary ranges for oxidation/reduction potentials of a charging redox mediator in, for example, a Mn/Zn battery cell, may include –0.2V to –0.1V versus Standard Hydrogen Electrode (SHE), –0.2V to 0V vs SHE, –0.2V to 0.1V vs SHE, –0.2V to 0.2V vs SHE, and −0.2V to 0.3V vs SHE, among other ranges, for Mn charging. Exemplary ranges also include −1.25V to −1.25V vs SHE, and −1.25V to −1.29V vs SHE, among other ranges, for Zn charging. Exemplary ranges for oxidation/reduction potentials for a discharging redox mediator in, for example, a Mn/Zn battery cell, may include −0.2V to −0.4V vs SHE, −0.2V to −0.6V vs SHE, and −0.2V to −0.8V vs SHE, among other ranges, for Mn discharging. Exemplary ranges also include −1.26V to −1.24V vs SHE, −1.26V to −1.22V vs SHE, −1.26V to −1.2V vs SHE, −1.26V to −1.1V vs SHE, and −1.26V to −1.0V vs SHE, among other ranges, for Zn discharging.

Examples of redox mediators include inorganic compounds and organic compounds. Exemplary inorganic compounds include metal halogen salts, metal oxohalide salts, metal ammonia complexes, metal cyanide salts, and metal oxide/hydroxide salts, among other kinds of inorganic compounds. Exemplary metal halogen salts include salts having the formula $M_nX_y$, where M represents one or more metals, X represents one or more halogens, n ranges from 1 to 5, and y ranges from 1 to 8. Exemplary metals M may include one or more metals chosen from iron, vanadium, titanium, manganese, cobalt, nickel, tin, copper, chromium, zinc, zirconium, cerium, iridium, ruthenium, osmium, and tungsten, among other metals. X represents halogens chosen from fluorine, chlorine, bromine, and iodide. Specific examples of metal halogen salts include iron chloride, titanium chloride, tin chloride, manganese chloride, cobalt chloride, iridium bromide, tungsten fluoride, tungsten chloride, vanadium chloride, and ruthenium iodide, among other metal halogen salts. Exemplary metal oxohalide salts include salts having the formula $M_nX_yO_z$, where M represents one or more metals, X represents one or more halogens, O represents oxygen, n ranges from 1 to 5, y ranges from 1 to 8, and z ranges from 1 to 5. Specific examples of metal oxohalide salts include metal hypochlorite salts ($M_n(ClO)_y$,) such as iron hypochlorite ($Fe(ClO)_2$) and titanium hypochlorite ($Ti(ClO)_4$), among other metal oxohalide salts. Exemplary metal ammonium complexes include complexes having the formula $M_n(NH_3)_y$, where M represents one or more metals, $NH_3$ represents ammonia ligands, n ranges from 1 to 5, and y ranges from 1 to 8. Exemplary metal cyanide salts include salts having the formula $M_n(CN)_y$, where M represents one or more metals, CN represents cyanide, n ranges from 1 to 5, and y ranges from 1 to 8. Specific examples of metal cyanide salts include iron cyanide, and tungsten cyanide, among other metal cyanide salts. Exemplary metal oxide/hydroxide salts include salts having the formula $M_nO_y$ and $M_n(OH)_y$, where M represents one or more metals, O represents oxygen (i.e., oxide ligand), OH represents hydroxide (i.e., hydroxide ligand), n ranges from 1 to 5, and y ranges from 1 to 8. Specific examples of metal oxide/hydroxide salts include titanium oxide, vanadium oxide, iron hydroxide, and cobalt hydroxide, among other metal oxide/hydroxide salts.

Examples of redox mediators include organic compounds such as quinone compounds, 2,2,6,6-tetramethylpiperidin 1-oxyl (TEMPO) compounds, triphenyl amine compounds, tetrathiafulvalene (TTF) compounds, tetracyanoquinodimethane (TCNQ) compounds, oxalate compounds, polyazamacrocycle compounds, polyamine compounds, polypyridyl compounds, tertiary amine compounds, porphyrin compounds, and salen compounds, among other types of organic compounds. Additional examples of organic redox mediators include heterocyclic nitrogen-substituted aliphatic and aromatic compounds such as pyridine compounds, tacn compounds, cyclen compounds, cyclam compounds, porphyrin compounds, and salen compounds, among others. In the redox mediator-containing electrolytes, these organic compounds may be complexed with metal ions.

Additional examples of redox mediators include polycarboxylic acids, such as dicarboxylic acids, tricarboxylic acids, tetracarboxylic acids, pentacarboxylic acids, hexacarboxylic acids, heptacarboxylic acids, octacarboxylic acids, nonacarboxylic acids, decacarboxylic acids, ect. Specific examples of polycarboxylic acid redox mediators include oxalic acid, malonic acid, succinic acid, fumaric acid, maleic acid, citraconic acid, itaconic acid, tartaric acid, glutaric acid, adipic acid, pimelic acid, suberic acid, azelic acid, phthalic acid, citric acid, isocratic acid, acontic acid, propane-1,2,3-tricarboxylic acid, trimesic acid, ethylenetetracarboxylic acid, furantetracarboxylic acid, and propane 1,1,3,3-tetracarboxylic acid, among others.

Additional examples of redox mediators include polyamine compounds such as diamines, triamines, tetramines, pentaamines, hexamines, ect. Exemplary polyamine compounds include compounds with structural formulas such as:

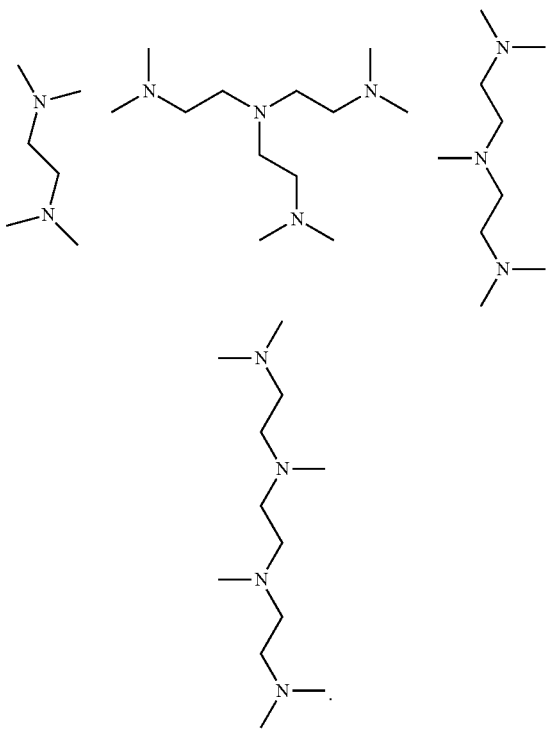

Additional examples of redox mediators include substituted monocyclic aromatic compounds such as compounds with structural formulas:

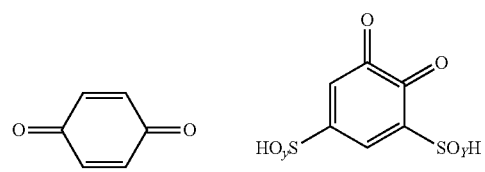

-continued

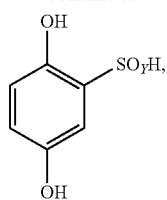

where y independently represents and integer of 1, 2, or 3.

Additional examples of redox mediators include nitrogen-and-phenyl-containing compounds such as aromatic amines. Specific examples of nitrogen-and-phenyl-containing compounds include compounds with structural formulas such as:

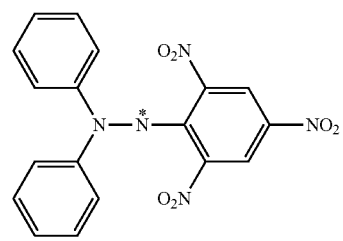

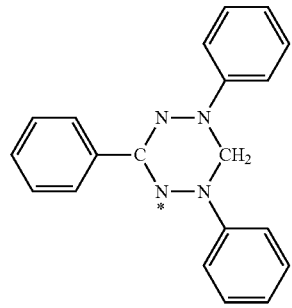

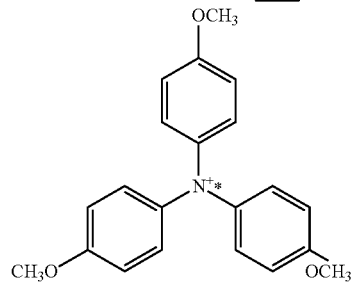

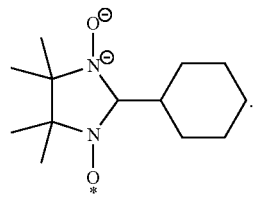

Additional examples of redox mediators include nitrogen-containing, heterocyclic aromatic compounds such as pyridine compounds, quinoline compounds, and isoquinoline compounds, among other nitrogen-containing, heterocyclic aromatic compounds. Exemplary compounds include compounds with structural formulas such as:

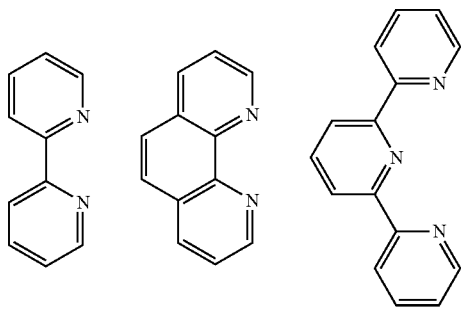

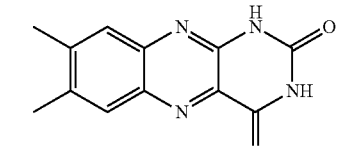

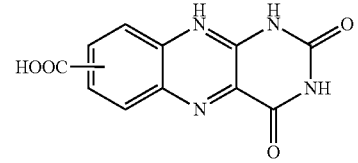

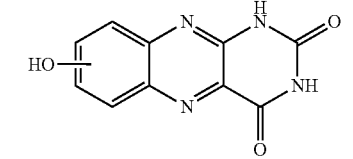

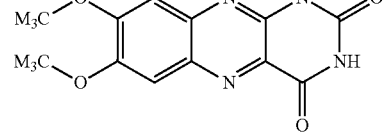

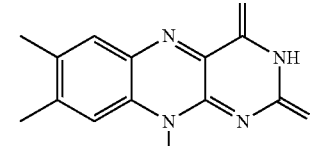

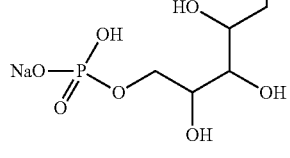

Additional examples of redox mediators include anthraquinone compounds such as hydroxyl-substituted anthraquinones, sulfate-substituted anthraquinones, and hydroxyl-and-sulfate substituted anthraquinones, among others. Exemplary anthraquinone compounds include compounds with structural formulas such as:

Additionally examples of redox mediators include anthraquinone compounds such as hydroxyl-substituted anthraquinones, sulfate-substituted anthraquinones, and hydroxyl-and-sulfate substituted anthraquinones, among others. Exemplary anthraquinone compounds include compounds with structural formulas such as:

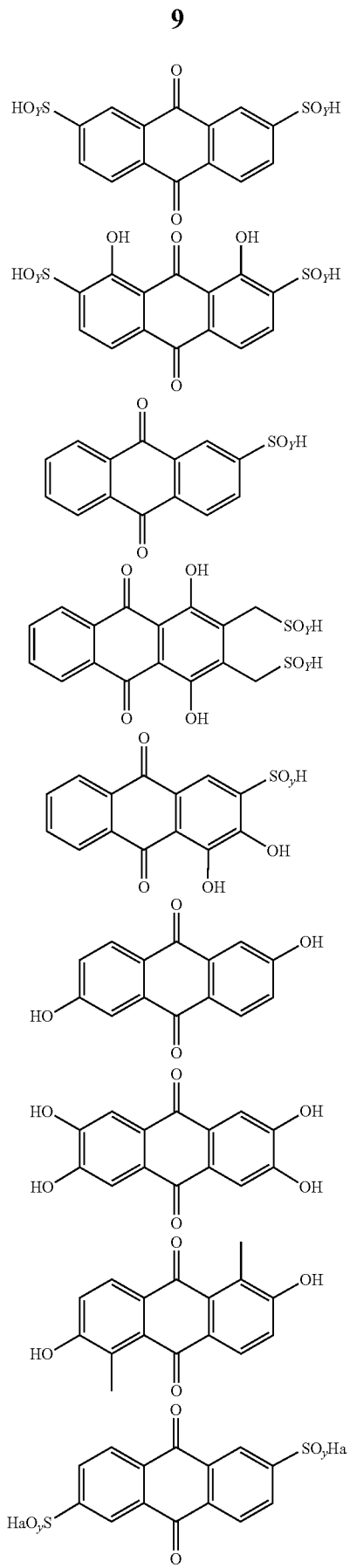

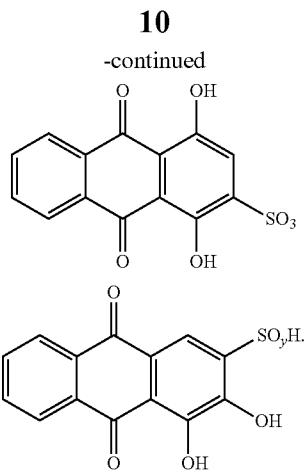

Additional examples of redox mediators include TEMPO compounds having structural formulas such as:

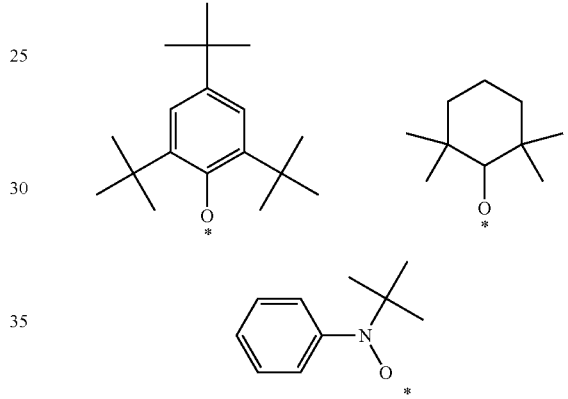

Additional examples of redox mediators include heterocyclic nitrogen-containing compounds such as tacn compounds, cyclen compounds, cyclam compounds, porphyrin compounds, and salen compounds, among others. Exemplary heterocyclic nitrogen-containing compounds include compounds with structural formulas such as:

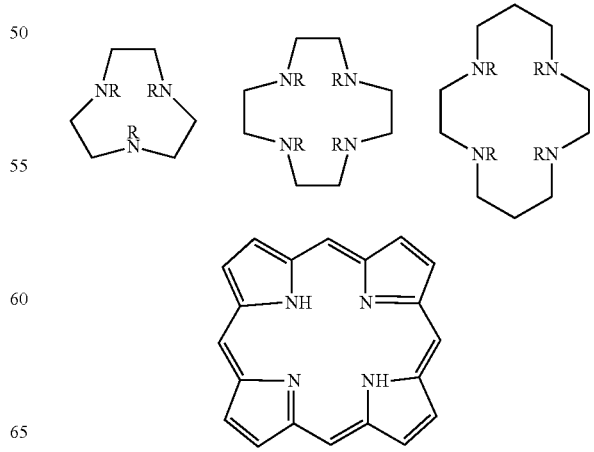

-continued

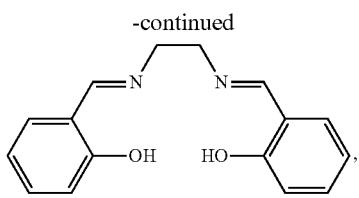

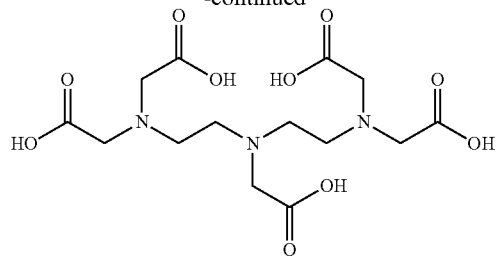

where each R may independently represent hydrogen, a hydroxyl group, an alcohol group, an alkoxy group, an alkyl group, or a carboxyl group. Examples also include carboxyl-group substituted heterocyclic nitrogen-containing compounds such as compounds with structural formulas like:

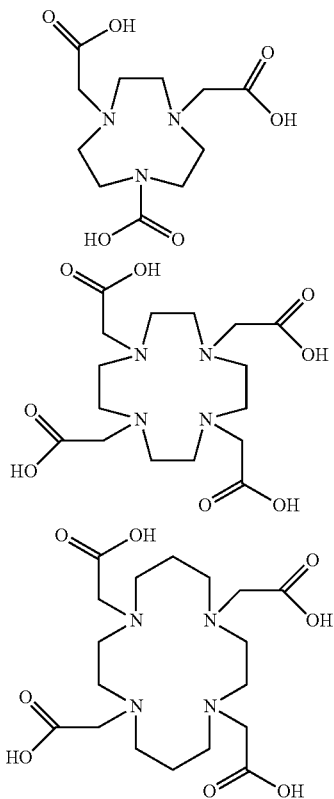

Examples also include carboxyl-group substituted nitrogen-containing compounds such as compounds with structural formulas like:

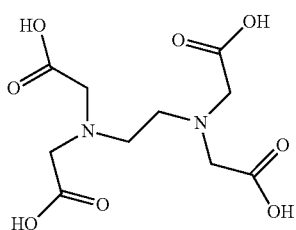

Additional examples of redox mediators include triphenyl compounds. Exemplary triphenyl compounds include compounds with structural formulas such as:

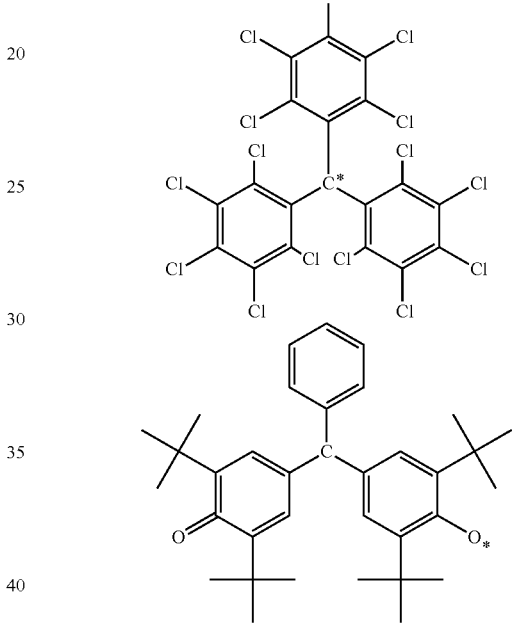

Additional examples of redox mediators include tricyclic aromatic compounds such as anthracene, phenanthrene, and aceheptylene, among others. Exemplary tricyclic aromatic compounds include compounds with structural formulas such as:

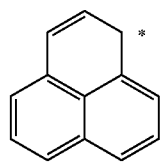 [SMILES: C1=Cc2cccc3cccc(c23)C1]

In some embodiments, the redox mediator-containing electrolyte may include one or more additional electrolyte additives. These additional electrolyte additives may include wetting agents, chelators, corrosion inhibitors, organic compounds, metal oxide/hydroxide compounds, and inorganic salts, among other classes of electrolyte additives. In some instances, an electrolyte additive can fall into two or more classes, such as an organic compound that can also act as a wetting agent (e.g., methanol), or a metal hydroxide that is also an inorganic salt (e.g., calcium hydroxide). In exemplary redox mediator-containing electrolytes where the electrolyte additive can also function as a hydroxide salt dissolved in the water, the one or more hydroxide salts have a different composition than the electrolyte additive (e.g., the hydroxide salt dissolved in the water is potassium hydroxide (KOH) while the metal oxide/hydroxide electrolyte additive does not include potassium hydroxide).

Examples of electrolyte additives that are wetting agents may include $C_1$-$C_6$ alcohols such as methanol, ethanol, propanol, isopropyl alcohol, butanol, t-butanol, pentanol, and hexanol, among other alcohols. Exemplary wetting agents may also include diol, triols, and polyols, such as polyvinyl alcohol.

Examples of electrolyte additives that are chelators include compounds that can function to sequester one or more types of metal-containing ions (e.g., zinc-containing ions, manganese-containing ions, etc.) in the electrolyte. Exemplary chelators include carboxylic acid-containing compounds, amine-containing compounds (e.g., polyamines, amine alcohols, amine sulfonates), alcohol-containing compounds (e.g., polyols), and imine-containing compounds (e.g., polyethyleneimines), among other compounds. Exemplary carboxylic acid-containing chelators include polyacetic acids such as tetraacetic acid, ethylenediaminetetraacetic acid (EDTA), and diethylenetriaminepentaacetic acid (DTPA), and nitrilotriacetic acid. Exemplary carboxylic acid-containing chelators also include lactic acid and oxalic acid. Exemplary amine-containing chelators include barium diphenylamine-4-sulfonate, and triethanolamine. Exemplary chelators may also include nitrogen-containing compounds such as mercaptothiadiazole, mercaptothiazole, and pyrimidine. Exemplary alcohol-containing chelators include glycerol.

Examples of electrolyte additives that are corrosion inhibitors may include amino acids such as glycine and alanine (e.g., L-alanine), and alcohol amines such as monoethanol amine, and triisopropanolamine, among other compounds. Exemplary corrosion inhibitors may include cyclic organic compounds such as thiazole compounds (e.g., benzothiazole and 2-mercaptobenzothiazole, 4-methyl-5-thiazoleethanol), pyridine compounds such as 4-hydroxypyridine, oxazole compounds such as benzoxazole, thiadiazole compounds such as 2,1,3-benzothiadiazole, pyrazole compounds such as pyrazole and methylpyrazole, pyrrole compounds such as pyrrole, pyrrolidone compounds such as polyvinyl pyrrolidone, pyrazine, phenazine, triazole compounds such as benzotriazole and 3-amino-1,2,4,-triazole-5-thiol, alginic acid salts (e.g., algenates), among others. Exemplary corrosion inhibitors may include polycyclic ring compounds such as indole, quinazoline, and quinolines (e.g., 8-hydroxyquinoline), among others. Exemplary corrosion inhibitors may include purine-containing compounds such as purine, adenine, guanine, xanthine, uric acid, caffeine, and hypoxanthine, among others. Exemplary corrosion inhibitors may include carboxylic acids (and their salts) such as glycolic acids (glycolates), alginic acids (e.g., algenates), pectic acids (e.g., pectates), and benzoic acids (e.g., sodium benzoate), among others.

Examples of electrolyte additives that are organic compounds include piperonal, and veratraldehyde, among others. Exemplary organic compounds may also include polyethylene glycols (PEGs). In some embodiments, the PEG may have a molecular number ($M_n$) ranging from 100 to 5000 (e.g., PEG-200, PEG-600, PEG-1200, etc.).

Examples of electrolyte additives that are metal oxide/hydroxide compounds may include group 1-16 metal oxides and hydroxides. Examples of these metal oxide/hydroxide compounds may include aluminum(III) hydroxide, bismuth (III) oxide, titanium(II) oxide, titanium(IV) oxide, barium (II) hydroxide, lead(IV) oxide, iron(II) oxide, iron(III) oxide, iron(II, III) oxide, silver(I) oxide, indium(III) oxide, magnesium(II) hydroxide, tantalum(V) oxide, tungsten(IV) oxide, tungsten(VI) oxide, molybdenum(IV) oxide, nickel (II) hydroxide, manganese(II) oxide, manganese(III) oxide, manganese(IV) oxide, manganese(II) hydroxide, tin(II) oxide, tin(IV) oxide, cobalt(II) hydroxide, zirconium(IV) oxide, copper(II) oxide, copper(II) hydroxide, calcium oxide, calcium hydroxide, strontium hydroxide, vanadium oxide, chromium oxide, zinc oxide, zinc hydroxide, gallium hydroxide, and lithium hydroxide, among other metal oxides and hydroxide compounds. It should be appreciated that when these metal oxide/hydroxide compounds are incorporated into the electrolyte, they may undergo hydration and/or ionization reactions in the highly-alkaline electrolyte. For example, the metal oxide/hydroxide may be transformed into a metal-hydroxide ion in the electrolyte. It should also be appreciated that when a metal oxide/hydroxide compound is incorporated as an electrolyte additive in the electrolyte, it is a different compound than the at least one hydroxide salt dissolved in the water of the electrolyte to make an aqueous alkaline solution. For example, if the hydroxide salt is potassium hydroxide (KOH), then the metal oxide/hydroxide compound is a compound other than KOH.

Examples of electrolyte additives that are inorganic salts include salts having at least one cation chosen from $Li^+$, $K^+$, $Na^+$, and $Cs^+$; and at least one anion chosen from $F^-$, $Cl^-$, $Br^-$, $I^-$, $NO_3^-$, $BO_3^{3-}$, $B_4O_7^{2-}$, $CO_3^{2-}$, $SO_4^{2-}$, $SiO_3^{2-}$, $S_2O_3^{2-}$, $S_2^-$, $SnO_3^{2-}$, $OAc^-$, or $PO_4^{3-}$. Oxide (e.g., $O^{2-}$) and/or hydroxide (i.e., $OH^-$) anions may be excluded from the electrolyte additive inorganic salts. This does not mean, however, that the electrolyte must lack an oxide and/or hydroxide-containing inorganic salt: these salts may be added as, for example, a hydroxide salt dissolved in the water and/or a metal oxide/hydroxide compound incorporated as an electrolyte additive into the water of the electrolyte. Specific examples of electrolyte-additive inorganic salts include LiF, KF, KCl, KBr, $K_2SiO_3$, $K_2B_4O_7$, $K_2CO_3$, $K_2SO_4$, $K_3PO_4$, and $KNO_3$, among other inorganic salts.

In some instances, the redox mediator may have additional functions in the redox mediator-containing electrolyte. For example, the redox mediator may also function as one or more of a wetting agent, a chelator, or a corrosion inhibitor, among other functions in the electrolyte. For example, redox mediators that include polyazamacrocycle compounds may also act as chelators.

Exemplary Effects of Redox Mediator-Containing Electrolytes on Cell Performance

The above-described redox mediator-containing electrolytes can affect many different battery cell performance characteristics including the rate capability of the battery cell and/or the cycle life of the battery cell. The rate capability of the battery cell may be evaluated by comparing capacity, typically measured in mAh/g, at two or more different charge and/or discharge rates, typically described as a multiple of the C-Rate. The cycle life of the battery cell may be evaluated by comparing capacity over a range of charging and discharging cycles for the battery cell. In some comparisons, the cycle lifetime is expressed as a percentage of the initial capacity of the battery cell after a fixed number of charge/discharge cycles (e.g., 20 cycles, 50 cycles, 60 cycles, 100 cycles, 200 cycles, 300 cycles, 500 cycles etc.). In additional comparisons, the cycle lifetime is expressed as the cycle number where the capacity decreases to 80% of the initial capacity (e.g., 5 cycles, 20 cycles, 50 cycles, 60 cycles, 100 cycles, 200 cycles, 300 cycles, 500 cycles etc.).

The redox mediator-containing electrolytes can improve the battery cell's performance characteristics by increasing at least one of the battery cell's rate capability and/or the battery cell's cycle life. For example, a battery cell that includes an electrolyte with one or more of the above-described redox mediators may have an increased rate capability of at least 10% relative to a battery cell that has an electrolyte which does not include the one or more redox mediators, but is otherwise identical. Similarly, a battery cell that includes an electrolyte with one or more of the above-described redox mediators may have an increased cycle life of at least 10% relative to a battery cell that has an electrolyte which does not include the one or more redox mediators, but is otherwise identical.

In some embodiments, the redox mediator-containing electrolytes can improve (e.g., increase) one or more of the battery cell's performance characteristics by at least 11%, 12%, 13%, 14%, 15%, 16% 17%, 18%, 19%, 20%, 21%, 22%, 23%, 24%, 25%, 30%, 35%, 40%, 45%, 50%, 55%, 60%, 65%, 70%, 80%, and 90%, among other threshold levels. Additional ranges include 10% to 100%, 15% to 90%, 20% to 80%, and 30% to 50%, among other exemplary ranges.

Exemplary Energy Storage Devices

The above-described redox mediator-containing electrolytes may be incorporated into energy storage devices such a battery cells that have a positive electrode and a negative electrode. The materials used in the electrodes and the electrolyte can classify the type of battery cell. For example, battery cells having a $MnO_2$-containing positive electrode (sometimes referred to as a cathode electrode when the battery cell is discharging) and an alkaline aqueous electrolyte may be classified as an alkaline battery cell. An $MnO_2$-containing positive electrode has electrode active materials that may include manganese-containing compounds that undergo redox reactions between an oxidized compound (e.g., $MnO_2$) and more reduced compound (e.g., $Mn(OH)_2$) during the charge and discharge cycles of a secondary alkaline battery cell. In some embodiments, the alkaline battery cell includes a zinc-containing negative electrode. These negative electrodes have electrode active materials that include zinc-containing compounds which undergo redox reactions between a reduced compound (e.g., Zn metal) and a more oxidized compound (e.g., $ZnO_2$) during the charge and discharge cycles of a secondary alkaline battery cell.

In many embodiments, the battery cell also includes an ion-selective material that may slow or prevent the migration of one or more electrolyte additives from a particular component or group of components in the battery cell. In some embodiments, the battery cell may also include a separator to electrically insulate the electrode from each other and prevent an electrical short. In additional embodiments, the ion-selective material may be sufficiently electrically insulating to replace a discrete separator in the battery cell. Example materials that may be used in the ion-selective material and the electrodes are now discussed.

Exemplary Ion-Selective Materials

The ion-selective materials are formulated to selectively provide efficient anionic transport of hydroxide ions across the material while selectively limiting transport of other neutral and ionic species such as those generated by the electrolyte additives. The blocked neutral and ionic species may include one or more species generated from the wetting agents, chelators, corrosion inhibitors, organic compounds, metal oxides/hydroxides, and inorganic salts used as electrolyte additives. For example, metal-containing species generated by the electrolyte additives such as metal containing cations, metal-containing anions, and/or metal-containing ionic complexes may be selectively slowed or stopped from passing though the ion-selective materials (e.g., an ion-selective barrier) while at the same time hydroxide ions from the alkaline electrolyte can pass through the material. The ion-selective materials may include one or more ion-selective polymers. The ion-selective materials may be incorporated into a separator between the negative and positive electrode, coupled to a separator, replace the separator, coated on at least one of the negative electrode and positive electrode, and/or incorporated into the negative electrode material and/or the positive electrode material.

The ion-selective materials may have a hydroxide ion conductivity of at least 1 mS/cm, while also having a diffusion ratio of the hydroxide ions to one or more type of ions that are selected to be blocked (e.g., a metal-containing ion complex) of at least about 10:1. Additional exemplary ranges for the hydroxide ion conductivity include at least about 2 mS/cm, at least about 5 mS/cm, at least about 10 mS/cm, at least about 25 mS/cm, at least about 50 mS/cm, at least about 75 mS/cm, at least about 100 mS/cm, at least about 125 mS/cm, at least about 150 mS/cm, at least about 175 mS/cm, at least about 200 mS/cm, etc. Exemplary hydroxide ion conductivity ranges include about 50 mS/cm to about 200 mS/cm, and about 100 mS/cm to about 200 mS/cm, among other ranges. Additional exemplary ranges for the diffusion ratio of the hydroxide ions to one or more type of ions that are selected to be blocked include at least about 100:1, at least about 1,000:1, at least about 10,000:1, at least about 100,000:1, at least about 1,000,000:1, etc. The diffusion ratio may also be 1:0 in which case the hydroxide ions are permeable to the ion-selective material while the ions that are selected to be blocked cannot pass through the material. Exemplary diffusion ratio ranges of hydroxide ions relative to the ions selected to be blocked include about 10:1 to about 10,000:1, about 100:1 to about 10,000:1, about 1000:1 to about 10,000:1, among other ranges.

The ion-selective materials include ion-selective polymers. Exemplary polymers or polymeric materials may include one or more base monomers or materials with which one or more functional groups may be incorporated. For example, base materials may include one or more repeating moieties in any combination, and may include compounds or groups including hydrocarbons including alkanes, alkenes, or alkynes that may be linear, branched, aromatic, and may include, for example polypropylene including unsaturated polypropylene, polyethylene including unsaturated polyethylene, polyphenylene, polystyrene, or other organic polymers. The base materials may also include one or more substituted elements including a substituted pnictogen, chalcogen, or halogen, for example. The base materials may include one or more carbonyl or sulfonyl groups. Exemplary base materials may be or include poly(arylene ethers), polyether ketones, polyaryl ether ketones, polyether ether ketone, polyether sulfones, polysulfones that may include cardo, phythalazinone, fluorenyl, or other groups, polyetherimides, polybenzimidazoles, polyether oxadiazoles, polyphenylene oxides, polyvinyl chlorides including polyvinyl benzyl chloride, polyphosphazenes, polyepichlorohydrins, organofluorine compounds including fluorocarbons and perfluorinated materials, hydrofluorocarbons, or other fluoropolymers. Additional materials may be used as the base, which may be characterized by properties similar to any of the noted materials, or other properties which may facilitate hydroxide conduction as explained elsewhere throughout the disclosure.

Coupled with one or more of the base materials may be one or more functional groups, which may extend from a base material, connect multiple base materials or functional groups, or may otherwise be associated with the base materials. The functional group may be characterized by a positive charge, and may include one or more materials including a tetral, pnictogen, chalcogen, or combination of materials, which may also include a metal-containing material, such as a transition-metal-containing cationic group. Exemplary materials may include ammoniums, phosphoniums, sulfoniums, any of which may be or include permanently charged cationic groups such as quaternary cationic compounds. For example, functional groups may include ammoniums including quaternary ammoniums, alkyl-bound ammoniums including benzyl trialkylammoniums, guanidine groups including alkyl or aryl groups, quinuclidine groups including quinuclidine-based quarternary ammoniums, bicyclic, tricyclic, and other heterocyclic ammonium groups, imidazoliums or benzimidazoliums, 1,4-diazabicyclo[2.2.2]octane based groups which may include one or multiple quarternary ammoniums, alkali-stabilized phosphonium groups including quarternary phosphonium groups, phosphorous-nitrogen-containing groups, phosphorous-nitrogen-sulfur-containing groups, metal-nitrogen groups, metal-phosporous groups, as well as combinations of these materials. The functional groups may be characterized by a +1 charge, or may be characterized by a +2 charge, +3 charge, or higher charge.

Also coupled with the base material may be a crosslinker that crosslinks two or more polymers of the base material together. The crosslinker includes two or more reactive groups operable to bond with the base material polymers. For example, a first reactive group of the crosslinker can bond with a reactive counterpart on a first polymer of the base material and a second reactive group of the crosslinker can bond with a reactive counterpart of a second polymer of the base material. Some crosslinkers may include a third, fourth, fifth, etc., reactive group operable to bind with reactive counterparts on additional polymers of the base material. Crosslinking together the polymers of the base material with the crosslinker can mechanically strengthen the polymeric material in applications like a battery separator. On a smaller scale, crosslinking together the polymers of the base material can reduce the size of pores though which ions in the electrolyte migrate between the positive electrode and negative materials of the battery cell. Because ions like hydroxides and hydrogen ions are significantly smaller than the neutral and ionic species generated by the electrolyte additives, crosslinking the polymers of the base material can increase the selectivity of the polymeric material for hydroxide ion transport over transport of the electrolyte additive species.

Exemplary crosslinkers for the polymeric materials can include organic crosslinkers such as divinylbenzene, tetramethylguanidine, and 4-tert-butylcatechol-2a, among others. Exemplary crosslinkers for the polymeric materials can also include inorganic crosslinkers such as polyvalent metal oxides like titanium oxide and zirconium oxide, among other inorganic crosslinkers. The crosslinkers may be added in amounts ranging from about 1 wt. % to about 30 wt. % of the base polymer material. Additional exemplary ranges include about 1 wt. % to about 20 wt. % of the base polymer material, about 1 wt. % to about 10 wt. % of the base polymer material, about 5 wt. % to about 30 wt. % of the base polymer material, among other amounts.

The ion-selective polymeric material may be structured or configured to afford distribution of hydroxide ions and/or water across the polymeric material. The polymeric material may also be structured or configured to limit cations or metal ions from passing through the structure. For example, the polymeric material may be configured to limit zinc-containing ions, manganese-containing ions, iron-containing ions, vanadium-containing ions, titanium-containing ions, and/or other metal-ions of an electrode material from passing through the polymeric material. The mechanisms by which hydroxide ions and/or water may pass through the structure may include voids or chain structures that permit permeability of water through the structure, and may permit hydroxide ions to permeate through the polymeric material. In some embodiments, although water may permeate through the polymeric structure, anions and cations from the electrode half reactions may not diffuse through the polymeric structure, and hydroxide ions may be passed across the structure via a different mechanism.

For example, the polymeric material may also include hydroxide ions associated with the polymer structure. The polymeric material may be functionalized to include hydroxide ions with the structure that may be bonded or associated with the structure. The hydroxide ions may be exchanged through the structure when hydroxide ions released during an electrode reaction contact or interact with the polymeric material. For example, as a hydroxide ion interacts with a first outer surface of the polymeric material as they are formed from a first reaction within the battery at one electrode, an internal hydroxide ion within the polymeric material may be dislocated, which may interact with an additional portion of the polymeric material. This interaction may dislocate an additional hydroxide ion, which may continue through the structure until a hydroxide ion is dislocated at a second outer surface of the polymeric material opposite the first outer surface. The released hydroxide ion from the second outer surface may pass through the separator and interact with the opposite electrode. Any number of dislocations may occur, including a single hydroxide release from a second surface opposite a first surface that is contacted by a hydroxide ion.

Examples of the ion-selective material include a single layer or sheet of the ion-selective polymeric material as shown in FIG. 1. The layer of polymeric material may be characterized by a thickness through the polymeric material of less than or about 0.5 mm in embodiments, and may be characterized by a thickness of less than or about 0.25 mm, less than or about 0.20 mm, less than or about 0.15 mm, less than or about 0.10 mm, less than or about 0.07 mm, less than or about 0.05 mm, less than or about 0.03 mm, less than or about 0.01 mm, or less. The layer of polymeric material may retain certain mechanical properties to allow application along manufacturing lines. For example, the layer polymeric material may be characterized by a tensile or other strength in a machine direction of greater than or about 50 kg/cm$^2$ in embodiments, and may be characterized by a strength in a machine direction of greater than or about 100 kg/cm$^2$, greater than or about 150 kg/cm$^2$, greater than or about 200 kg/cm$^2$, greater than or about 250 kg/cm$^2$, greater than or about 300 kg/cm$^2$, greater than or about 350 kg/cm$^2$, greater than or about 400 kg/cm$^2$, greater than or about 450 kg/cm$^2$, greater than or about 500 kg/cm$^2$, greater than or about 550 kg/cm$^2$, greater than or about 600 kg/cm$^2$, greater than or about 650 kg/cm$^2$, greater than or about 700 kg/cm$^2$, greater than or about 750 kg/cm$^2$, or higher.

As noted above, the ion-selective material may be placed in various configurations between the positive and negative electrodes in the battery cell. FIGS. 2A-D show embodiments of some of the configurations of the ion-selective material. In FIG. 2A, the exemplary electrode pair 200 includes a negative electrode 202 and positive electrode 204 that are electrically separated by a separator 206 and a barrier of ion-selective material 208. In this embodiment, the barrier of ion-selective material 208 is a separate layer that contacts both the separator 206 and the positive electrode 204. In an alternate embodiment (not shown) the ion-selective material is incorporated into the separator 206 instead of being a separate layer 208 in contact with a surface of the separator 206. FIG. 2B shows another embodiment of an electrode pair 220 that includes the negative electrode 202 and positive electrode 204 electrically separated by the barrier of ion-selective material 208. In this embodiment, the barrier of ion-selective material 208 functions as both an ion barrier for the passage of select ions (e.g., hydroxide ions) between the electrodes and an electrical insulator to prevent an electrical short between the electrodes. FIG. 2C shows still another embodiment of an electrode pair 240 that includes the negative electrode 202 coated by a first layer of ion-selective material 210 and the positive electrode 204 coated by a second layer of ion-selective material 212. The first and second layers of ion-selective materials (210 and 212) may be made of the same ion-selective material or different ion-selective materials. In the embodiments shown, the first and second layers of ion-selective material function as both an ion-selective barrier and an electrical insulator that eliminates the need for a conventional separator between the electrodes. Alternate embodiments (not shown) include only one electrode being coated with a layer of ion selective material (e.g., positive electrode 204) and/or a separator positioned between the electrodes. FIG. 2D shows an electrode pair 260 that includes the negative electrode 202 and a positive electrode 214 positioned on opposite sides of a separator 206. In this embodiment, the positive electrode 214 has an ion-selective material incorporated into the positive electrode active material of the electrode. Alternate embodiments (not shown) include the incorporation of ion selective material into the negative electrode, and the elimination of a conventional separator between the electrodes. The embodiments of configurations of ion-selective material shown in FIG. 2A-D is non-exhaustive, and there are more configurations contemplated which are not described here.

Exemplary Positive Electrode Materials

Exemplary positive electrode materials may include manganese-containing compounds such as manganese dioxide ($MnO_2$), as well as other manganese-containing compounds that are generated when charging and discharging the positive electrode (e.g., MnOOH, $Mn(OH)_2$, $Mn_3O_4$, etc.). In some embodiments, the positive electrode materials may also include a conductive carbon material (e.g., graphite, carbon nanotubes, etc.), a binder for the electrode materials (e.g., an organic polymer binder), and one more metal-containing additives that may be incorporated as compounds and/or dopants in the positive electrode materials. These metal-containing additives may include one or more additives chosen from iron-containing (Fe) compounds and/or dopants, vanadium-containing (V) compounds and/or dopants, antimony-containing (Sb) compounds and/or dopants, titanium-containing (Ti) compounds and/or dopants, silver-containing (Ag) compounds and/or dopants, aluminum-containing (Al) compounds and/or dopants, barium-containing (Ba) compounds and/or dopants, bismuth-containing compounds and/or dopants, calcium-containing (Ca) compounds and/or dopants, chromium-containing (Cr) compounds and/or dopants, cobalt-containing (Co) compounds and/or dopants, copper-containing compounds and/or dopants, gallium-containing (Ga) compounds and/or dopants, germanium-containing (Ge) compounds and/or dopants, hafnium-containing (Hf) compounds and/or dopants, indium-containing (In) compounds and/or dopants, lanthanum-containing (La) compounds and/or dopants, magnesium-containing (Mg) compounds and/or dopants, molybdenum-containing (Mo) compounds and/or dopants, niobium-containing (Nb) compounds and/or dopants, nickel-containing (Ni) compounds and/or dopants, phosphorous-containing (P) compounds and/or dopants, lead-containing (Pb) compounds and/or dopants, silicon-containing (Si) compounds and/or dopants, tin-containing (Sn) compounds and/or dopants, strontium-containing (Sr) compounds and/or dopants, tantalum-containing (Ta) compounds and/or dopants, tungsten-containing (W) compounds and/or dopants, yttrium-containing (Y) compounds and/or dopants, zinc-containing (Zn) compounds and/or dopants, and zirconium-containing (Zn) compounds and/or dopants. Exemplary metal-containing compounds and/or dopants may include elemental compounds (e.g., metals), metal oxides, and metal hydroxides, among other metal-containing compounds. Some embodiments of the positive electrode materials may also include an ion-selective material.

As noted above, the manganese-containing compounds may include manganese oxides (e.g., MnO, $MnO_2$, etc.) and manganese hydroxides (e.g., $Mn(OH)_2$, etc.). Exemplary manganese oxides include manganese dioxide that has a single phase or multiple phases. Exemplary phases of manganese dioxide ($MnO_2$) include electrolytically produced manganese dioxide (EMD), $\alpha$-$MnO_2$, $\beta$-$MnO_2$, $\gamma$-$MnO_2$, $\delta$-$MnO_2$, $\varepsilon$-$MnO_2$, and $\lambda$-$MnO_2$, among other phases of $MnO_2$. The $MnO_2$ in the positive electrode material may be sourced from, derived from, or accompanied by naturally occurring manganese oxides. These manganese oxides include hollandite (an $\alpha$-$MnO_2$), groutite (an $\alpha$-$MnO_2$), pyrolusite (a $\beta$-$MnO_2$), feitneichtite (a $\beta$-$MnO_2$), nsutite (a $\gamma$-$MnO_2$), manganite (a $\gamma$-$MnO_2$), birnessite (a $\delta$-$MnO_2$), akhtenskite (a $\varepsilon$-$MnO_2$), spinel (a $\lambda$-$MnO_2$), ramsdellite, todorokite, groutellite, psilomelane, and pyrochroite, among other types of manganese oxides. In some embodiments, the $MnO_2$ may have a purity of greater than 80 wt. %, greater than 85 wt. %, 90 wt. %, greater than 91 wt. %, greater than 92 wt. %, greater than 93 wt. %, based on the total weight of the $MnO_2$ material. Ranges of the $MnO_2$ purity level include 80 wt. % to 95 wt. %, 85 wt. % to 95 wt. %, and 90 wt. % to 95 wt. %, based on the total weight of the $MnO_2$ material. Exemplary limits on metal impurities in conventional, electrode-grade $MnO_2$ include less than 100 ppm Fe, less than 100 ppm Pb, and less than 5-7 ppm Ti, Cr, Ni, Co, Cu, V, Mo, As, and Sb. In some embodiments, these levels may be exceeded when the metal is incorporated into the positive electrode material as an additive (e.g., compound and/or manganese dopant) instead of being present as an impurity in the $MnO_2$.

The amount of $MnO_2$ in the positive electrode material can range from 30 wt. % to 98 wt. %. Additional exemplary ranges include 30 wt. % to 50 wt. %, about 70 wt. % to about 90 wt. %, about 35 wt. % to about 75 wt. %, about 30 wt. % to about 40 wt. %, and about 65 wt. % to about 75 wt. %, among other ranges. The amount of $MnO_2$ in the positive electrode material may depend on the intended use of the battery cell: for battery cells designed to favor specific power over energy density (e.g., VED) the positive electrode material may contain less $MnO_2$ (e.g., 30-50 wt. %) and more electrically conductive carbon (e.g., 10-20 wt. %). On the other hand, for battery cells designed to favor energy density over specific power, the positive electrode material may contain more $MnO_2$ (e.g., 70-90 wt. %) and less electrically conductive carbon (e.g., 1-10 wt. %).

For embodiments of positive electrodes that include electrically-conductive carbon, the electrically-conductive carbon may be one or more of natural graphite, synthetic graphite, expanded graphite, acetylene black, and carbon nanotubes (CNTs), among other types of electrically conductive carbon. The carbon may be added to the positive electrode materials in amounts ranging from about 0.1 wt. % to about 40 wt. % of the dry positive electrode material. The amount of added carbon depends in part on the target electrical conductivity of the positive electrode. $MnO_2$ is a relatively poor electrical conductor compared to electrically conductive carbon, so the carbon is added to lower the electrical resistance of the positive electrode and direct more energy from the battery cell's redox reactions to an external load instead of heating the battery cell. However, the benefits of loading the positive electrode material with electrically conductive carbon needs to be balanced with the reduction in volumetric energy density (VED) by replacing electrochemical active $MnO_2$ with electrochemically inactive carbon. As noted above, for battery cells designed to favor specific power (e.g., W/g) over volumetric/gravimetric energy density (e.g., Wh/L and Wh/g) the positive electrode material may contain less $MnO_2$ (e.g., 30-50 wt. %) and more electrically conductive carbon (e.g., 10-40 wt. %). On the other hand, for battery cells designed to favor energy density over specific power, the positive electrode material may contain more $MnO_2$ (e.g., 70-90 wt. %) and less electrically conductive carbon (e.g., 1-10 wt. %). In some instances, one or more electrically conductive metals may replace a portion of the electrically conductive carbon as an electrically conductive material in the positive electrode. In additional instances, one or more electrically conductive metals may replace all the electrically conductive carbon in the positive electrode to make the positive electrode free of electrically conductive carbon. Other carbon-containing compounds, for example organic compounds used in a binder or ion-selective material for the positive electrode or metal carbonate compounds, may still be present in a positive electrode that is free from electrically-conductive carbon.

For embodiments of positive electrodes that include a binder, the binder in the positive electrode material may include one or more organic polymers. Examples of these polymers include cellulose polymers such as ether cellulose polymers (e.g., alkyl cellulose polymers, hydroxyalkyl cellulose polymers, carboxyalkyl cellulose polymers, etc.). Exemplary alkyl cellulose polymers in the binder include methyl cellulose (MC) polymers, ethyl cellulose (EC) polymers, propyl cellulose (PC) polymers, etc. Examples of alkyl cellulose polymers also include combinations of two or more alkyl groups such as ethylmethyl cellulose polymers, propylmethyl cellulose polymers, etc. Examples of hydroxyalkyl cellulose polymers include hydroxymethyl cellulose (HMC), hydroxethyl cellulose (HEC), hydroxypropyl cellulose (HPC), etc. Examples of hydroxyalkyl cellulose polymers also include combinations of two or more alkyl groups such as hydroxyethylmethyl cellulose polymers, hydroxypropylmethyl cellulose polymers, etc. Examples of carboxyalkyl cellulose polymers include carboxymethyl cellulose (CMC), caroboxyethyl cellulose (CEC), caroboxypropyl cellulose (CPC), etc. Examples of carboxyalkyl cellulose polymers also include combinations of two or more alkyl groups such as carboxyethylmethyl cellulose polymers, carboxypropylmethyl cellulose polymers, etc. Additional examples of polymers in the binder include polyvinyl polymers such as polyvinyl alcohol (PVA), polyvinyl acetate (PVAc), polyacrylic acid polymers, polyethylene glycol polymers, polyvinylidene polymers. Still more examples of polymers in the binder include fluoropolymers such as polytetrafluoroethylene (sold under the tradename Teflon®) and polyvinylidene fluoride (PVDF). In some examples, the binder includes two or more types of polymers, such as a combination of a cellulose polymer and a vinyl polymer (e.g., a combination of carboxymethyl cellulose and polyvinyl alcohol). As discussed further below, the binder may include ion-selective materials (e.g., ion-selective polymers) that selectively control the diffusion of solubilized positive electrode materials out of the positive electrode.

For embodiments of the positive electrode that include a binder in the positive electrode materials, exemplary amounts of binder may range from about 0.1 wt. % to about 5 wt. % of the dry positive electrode material. Additional exemplary ranges for the binder in the positive electrode materials include 0.5 wt. % to 2 wt. %, 1 wt. % to 2 wt. %, 1 wt. % to 3 wt. %, 1 wt. % to 4 wt. %, and 1 wt. % to 5 wt. %, among other exemplary ranges. In some instances, the binder-containing positive electrode material may be treated to cure the binder. Exemplary treatments may include heating, drying, pressurizing, and/or exposing the binder-containing positive electrode material to UV light, among other treatments.

As noted above, the positive electrode materials contain at least one additive (e.g., compound and/or dopant), where the compound or dopant includes at least one element chosen from aluminum, antimony, barium, bismuth, calcium, chromium, cobalt, copper, gallium, germanium, indium, iron, lanthanum, magnesium, molybdenum, niobium, nickel, phosphorous, lead, silicon, silver, strontium, tin, tantalum, titanium, tungsten, vanadium, yttrium, zinc, and zirconium. These additives may be found in the positive electrode materials in elemental form (e.g., elemental metal), as oxides, and as hydroxides, among other compounds. Exemplary oxides include $M_xO_y$, where x and y are independently 1, 2, 3, 4, or 5, and M represents at least one element chosen from aluminum, antimony, barium, bismuth, calcium, chromium, cobalt, copper, gallium, germanium, indium, iron, lanthanum, magnesium, molybdenum, niobium, nickel, phosphorous, lead, silicon, silver, strontium, tin, tantalum, titanium, tungsten, vanadium, yttrium, zinc, and zirconium. Exemplary hydroxides include $M_x(OH)_y$, where x and y are independently 1, 2, 3, 4, or 5, and M represents at least one element chosen from aluminum, antimony, barium, bismuth, calcium, chromium, cobalt, copper, gallium, germanium, indium, iron, lanthanum, magnesium, molybdenum, niobium, nickel, phosphorous, lead, silicon, silver, strontium, tin, tantalum, titanium, tungsten, vanadium, yttrium, zinc, and zirconium. Exemplary additives include $Fe_2O_3$, $Bi_2O_3$, MgO, CaO, SrO, $Al_2O_3$, CuO, $Ga_2O_3$, $GeO_2$, $In_2O_3$, $SnO_2$, $Sb_2O_3$, $Cr_2O_3$, NiO, ZnO, $Y_2O_3$, $Nb_2O_5$, $MoO_3$, $HfO_2$, $ZrO_2$, $Ta_2O_5$, $WO_3$, $La_2O_3$, and $V_2O_3$, among other additives. Exemplary amounts of the additive in the positive electrode material include ranges of 1 wt. % to 20 wt. %, 1 wt. % to 15 wt. %, 1 wt. % to 10 wt. %, 1 wt. % to 5 wt. %, 1 wt. % to 4 wt. %, 1 wt. % to 3 wt. %, and 1 wt. % to 2 wt. %, among other exemplary ranges. Additional exemplary ranges include 2 wt. % to 5 wt. %, 3 wt. % to 5 wt. %, 4 wt. % to 5 wt. %, 5 wt. % to 10 wt. %, 5 wt. % to 15 wt. %, 10 wt. % to 20 wt. %, and 15 wt. % to 20 wt. %, among other exemplary ranges.

The one or more additives may be incorporated into the positive electrode material by, for example, doping the manganese-containing electrode material (e.g., manganese dioxide), adding the compounds in the positive electrode materials, incorporating the additives into the electrolyte that contacts the positive electrode, and/or incorporating the additives into a binder in the positive electrode materials, among other methods to incorporate the additives into the positive electrode material. In some examples, the one or more additives may be incorporated into the positive electrode material by two methods, three methods, four methods, etc. For example, an iron compound may be incorporated into the positive electrode material by both doping the manganese dioxide with the iron compound and incorporating the iron compound as an additive in the positive electrode material. In some examples, two or more metal compounds may be incorporated into the positive electrode materials by at least two different incorporation methods. For example, a first metal compound may be incorporated into the positive electrode material by a first method (e.g., doping the manganese dioxide with the first metal compound) while a second metal compound may be incorporated into the positive electrode material by a second method (e.g., incorporating the second metal compound as an additive in the electrolyte).

Positive electrodes made with positive electrode materials that include one or more of the additives can provide improved performance characteristics for secondary alkaline battery cells over similar battery cells with positive electrodes that lack the additives. These performance characteristics can include volumetric energy density (e.g., Wh/L), discharge/recharge cycle lifetime, and positive electrical conductivity (e.g., mS/cm), among other performance characteristics. The performance characteristics can be measured under various charging/discharging conditions such as C-rates, percentage depth of discharge (DoD), and temperature, among other conditions. These improved performance characteristics are maintained over an operational voltage range for an alkaline $MnO_2$/Zn battery cell (e.g., about 0.9 V to about 1.7 V). For example, the positive electrodes containing the additives can provide the battery cell with a volumetric energy density (VED) that ranges from about 60 Wh/L to about 700 Wh/L. Additional exemplary VED ranges include about 100 Wh/L to about 700 Wh/L, about 200 Wh/L to about 700 Wh/L, about 300 Wh/L to about 700 Wh/L, about 400 Wh/L to about 700 Wh/L, about 500 Wh/L to about 700 Wh/L, about 600 Wh/L to about 700 Wh/L, etc. The positive electrode containing the additives can provide the secondary battery cell with a charge/discharge cycle lifetime (i.e., cycles to reach 80% of initial capacity at 1C and 23° C.) of about 100 cycles to about 1500 cycles, about 150 cycles to about 1500 cycles, about 200 cycles to about 1500 cycles, about 300 cycles to about 1500 cycles, about 150 cycles to about 1200 cycles, about 300 cycles to about 1000 cycles, among other ranges of cycle lifetime. The positive electrode containing the additives can have an electrical conductivity ranging from about 50 mS/cm to about 200 mS/cm, about 100 mS/cm to about 200 mS/cm, about 150 mS/cm to about 200 mS/cm, etc. The positive electrode containing the additives can provide the secondary battery cell with an extended cycle lifetime under depths of discharge ranging from 10% to 100% of the battery cell's initial capacity. Exemplary ranges for the depth of discharge also include 25% to 100%, 30% to 100%, 40% to 100%, 50% to 100%, 60% to 100%, 25% to 80%, 30% to 80%, 40% to 80%, etc.

Exemplary Negative Electrode Materials

The negative electrode materials include one or more materials capable of conducting a negative half reaction with the manganese-containing material in the positive electrode through the alkaline aqueous electrolyte of the battery cell. Exemplary negative active materials include metallic zinc (Zn), nickel oxyhydroxide (NiOOH), and iron (Fe), among others. In some embodiments where metallic zinc (Zn) is the negative active material, the zinc is in powdered form and uniformly dispersed throughout the negative electrode with the aid of a gelling agent or binder that also facilitates the transport of hydroxide ions to and from the zinc particles during charge and discharge cycles. Exemplary gelling agents and binders include starches and their salts, cellulose polymers and their salts (e.g., carboxymethyl cellulose polymers), acrylic acid polymers and their salts (e.g., polyacrylates), olefinically-unsaturated anhydride polymers and their salts (e.g., maleic anhydride polymers), and olefinically-unsaturated aromatic polymers such as vinylbeneze polymers and their salts, among other gelling agents and binders. In some examples, the negative electrode material may include an ion-selective material which also functions as a gelling agent or binder. Exemplary particle size for the zinc powder ranges from about 20 μm to about 500 μm. In some instances, the zinc powder may include two or more different average size ranges of zinc particles (e.g., fine particles and coarse particles). In many examples, the zinc powder takes up the largest percentage weight of the negative electrode (e.g., about 60 wt. % to about 70 wt. %), and the aqueous alkaline electrolyte takes up the second largest percentage of the negative electrode's weight (e.g., about 25 wt. % to about 35 wt. %). Exemplary weights for the gelling agent or binder in these negative electrodes include about 0.4 wt. % to about 1 wt. %.

Embodiments of the negative electrode material may also include one or more hydrogen suppression agents to suppress the formation of hydrogen gas in the negative electrode. These suppression agents reduce the rate at which the metallic zinc in the negative electrode reduces water in the highly basic electrolyte to form zinc oxide and hydrogen gas. Exemplary hydrogen suppression agents include one or more metals such as metallic indium (In), lead (Pb), bismuth (Bi), and aluminum (Al). In some examples, these metals are alloyed with the metallic zinc. Exemplary hydrogen suppression agents include indium oxide ($In_2O_3$). Exemplary hydrogen suppression agents include organic compounds such as polyethylene glycol. Exemplary weight ranges for the hydrogen suppression agent include 0.01 wt. % to 1 wt. %, 0.01 wt. % to 0.1 wt. %, etc. The negative electrode material may be mercury free.

The suppression of hydrogen gas generation and metallic zinc oxidation may be maintained by controlling the amount of cathodic hydrogen generating compounds in the negative electrode. Exemplary compounds include metal-containing compounds and ions such as metallic iron and iron ions (e.g., $Fe(OH)_x^-$), metallic vanadium and vanadium ions (e.g., $VO(OH)_x^-$), metallic antimony and antimony ions ($Sb(OH)_x^-$), and titanium metal and titanium ions (e.g., $Ti(OH)_x^-$), among other compounds. These compounds are slowed or blocked from reaching the negative electrode by the ion-selective materials present in the battery cell. Exemplary amounts of these cathodic hydrogen generating compounds may include less than 4 ppm, less than 2 ppm, less than 1 ppm, less than 0.5 ppm, and less than 0.1 ppm, among other ranges. Exemplary ranges also include 4 ppm to 0.001 ppm, 3 ppm to 0.001 ppm, 2 ppm to 0.001 ppm, 1 ppm to 0.001 ppm, 0.5 ppm to 0.001 ppm, and 0.1 ppm to 0.001 ppm, among other ranges.

Exemplary Battery Cells

The redox mediator-containing electrolytes may be incorporated into a variety of different types of battery cells. A non-exhaustive list of these types of battery cells include plate-type battery cells, prismatic battery cells, pouch battery cells, cylindrical battery cells, and button battery cells, among other types of battery cells. Examples also include arrangements of multiple battery cells into larger batteries (a.k.a., modules) and still-larger battery packs (e.g., an arrangement of two or more batteries). A discussion of some of the above listed battery cell types follows.

Exemplary Plate-Type Battery Cells

Figure 3:
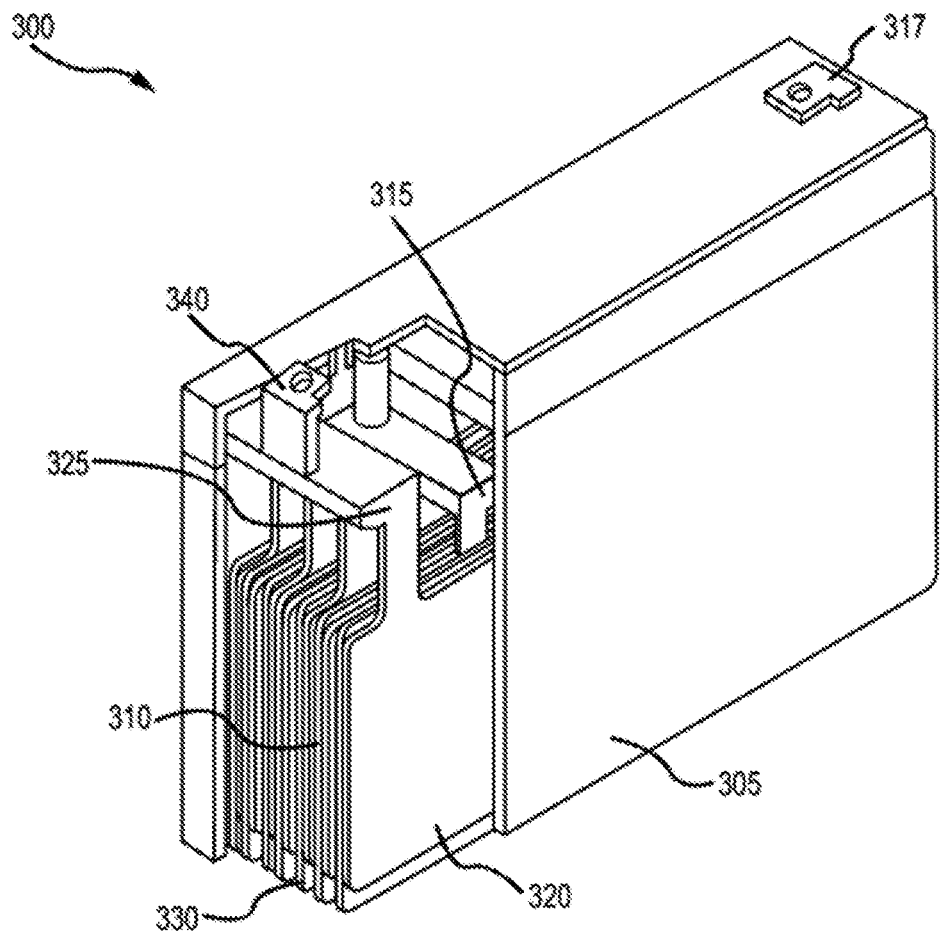
FIG. 3 shows a simplified schematic of a plate-type battery cell design that incorporates the present technology.

FIG. 3 shows a simplified schematic of a plate-type battery cell 300 that incorporates the present technology. Exemplary plate-type battery cell 300 may include an outer casing 305 that contains the components of the battery cell 300 including the electrolyte that acts as the transport medium for ion conduction between the positive electrode and negative electrode materials. Within the outer casing 305 may be at least one positive plate 310, that includes a positive electrode grid surrounded by the positive electrode material. The positive plate 310 may be formed by applying the positive electrode material as a slurry or paste to a mold that holds the positive electrode grid, and then processing the mold to form the positive plate 310. The positive electrode grid is made of electrically conductive materials (e.g., a conductive metal) that carries electrical current to and from the positive electrode material without significantly interfering with the electrochemical reactions of the positive active material (e.g., $MnO_2$) in the positive electrode material.

The positive electrode grid may extend beyond the positive electrode material to make electrical contact with the positive current collector 315. In additional examples, an extension of the electrode grid itself may form part of the current collector. The positive current collector 315 may be electrically coupled to an additional conductive element that is also coupled to other positive current collectors in the battery cell 300. A positive terminal 317 for battery cell 300 may be electrically coupled to the additional conductive element, or directly to the positive current collector 315. Positive current collector 315 may be stainless steel, or some other conductive material suitable for electronic transmission.

At least one negative plate 320 is also located within the outer casing 305 of the battery cell 300. Each negative plate 320 is formed from a negative electrode grid surrounded by an negative electrode material. The negative plate 320 may be formed by applying the negative electrode material as a slurry or paste to a mold that holds the negative electrode grid, and then processing the mold to form the negative plate 320. The negative electrode grid is made of electrically conductive materials (e.g., a conductive metal) that carries electrical current to and from the negative electrode material without significantly interfering with the electrochemical reactions of the negative active material (e.g., Zn) in the negative electrode material.

The negative electrode grid may extend beyond the negative electrode material to make electrical contact with the negative current collector 325. In additional examples, an extension of the electrode grid itself may form part of the current collector. The negative current collector 325 may be electrically coupled to an additional conductive element that is also coupled to other negative current collectors in the battery cell 300. A negative terminal 340 for battery cell 300 may be electrically coupled to the additional conductive element, or directly to the negative current collector 325. Negative current collector 325 may be stainless steel, or some other conductive material suitable for electronic transmission.

The positive plate 310 and negative plate 320 are ionically coupled through a separator 330 that also electrically insulates the plates from each other. The separator 330 permits the flow of hydroxide ions in an alkaline electrolyte between the positive plate 310 and negative plate 320 while preventing direct contact of the plates that could cause an electrical short circuit. The ion-selective materials discussed above may form the separator 330 or be incorporated onto or into separator 330 to prevent the flow of selected ionic species (e.g., metal-containing ionic species) between the positive plate 310 and negative plate 320. For example, the separator 330 may include an ion-selective polymeric material having a cationic backbone and one or more nitrogen-containing moieties in the structure. The backbone may include a hydrocarbon and/or a nitrogen-containing structure, or may include a derivative or benzene, such as styrene, or one or more polyolefin structural segments including one or more nitrogen-containing or other functional groups. Exemplary functional groups or moieties that may be incorporated within the structure include amines or other nitrogen-containing materials, which may be or include imidazole, anilenes, piperidinium, ammoniums, methylated nitrogen, or other nitrogen-containing materials or other non-metal materials, such as phosphoniums. The ion-selective polymeric material may be configured to provide anionic transport across the separator 330, while limiting cationic transport across the separator 330.

The ion-selective polymeric material may be structured or configured to afford distribution of hydroxide ions and/or water across the polymeric material. The ion-selective polymeric material may also be structured or configured to limit cations or metal ions from passing through the structure. For example, the ion-selective polymeric material may be configured to limit zinc-containing ions, manganese-containing ions, iron-containing ions, vanadium-containing ions, titanium containing ions, and/or other metal-ions in the electrode materials from passing through the ion-selective polymeric material. The mechanisms by which hydroxide ions and/or water may pass through the structure may include voids or chain structures that permit permeability of water through the structure, and may permit hydroxide ions to permeate through the ion-selective polymeric material. In some embodiments, although water may permeate through the separator 330, anions and cations from the electrode half reactions may not diffuse through the polymeric structure, and hydroxide ions may be passed across the separator 330 via a different mechanism.

For example, the ion-selective polymeric material may also include hydroxide ions associated with the polymer structure. The ion-selective polymeric material may be functionalized to include hydroxide ions with the polymeric material that may be bonded or associated with the polymeric material. The hydroxide ions may be exchanged through the polymeric material when hydroxide ions released during an electrode reaction contact or interact with the polymeric material. For example, as a hydroxide ion interacts with a first outer surface of the polymeric material as they are formed from a first reaction within the battery at one electrode, an internal hydroxide ion within the polymeric material may be dislocated, which may interact with an additional portion of the polymeric material. This interaction may dislocate an additional hydroxide ion, which may continue through the polymeric material until a hydroxide ion is dislocated at a second outer surface of the polymeric material opposite the first outer surface. The released hydroxide ion from the second outer surface may pass through the polymeric material and interact with the opposite electrode. Any number of dislocations may occur, including a single hydroxide release from a second surface opposite a first surface that is contacted by a hydroxide ion.

The ion-selective polymeric material may be characterized by a number of properties based on its structure. For example, the ion-selective polymeric material may be stable at pH conditions above 7 within the cell environment, and may be stable at conditions that may be highly basic, and may include pH conditions discussed above based on the electrolyte concentration, which may be up to or greater than a pH of 9, up to or greater than a pH of 10, up to or greater than a pH of 11, up to or greater than a pH of 12, up to or greater than a pH of 13, up to or greater than a pH of 14, up to or greater than a pH of 15, up to or greater than a pH of 16, up to or greater than a pH of 17, up to or greater than a pH of 18, or higher. The ion-selective polymeric material may also be characterized by a conductivity for hydroxide ions up to or about 1 mS/cm, and may be characterized by a conductivity for hydroxide ions greater than or about 2 mS/cm, greater than or about 5 mS/cm, greater than or about 10 mS/cm, greater than or about 25 mS/cm, greater than or about 50 mS/cm, greater than or about 75 mS/cm, greater than or about 100 mS/cm, greater than or about 125 mS/cm, greater than or about 150 mS/cm, greater than or about 175 mS/cm, greater than or about 200 mS/cm, or higher.

The ion-selective polymeric material may be characterized by a thickness through the polymeric material of less than or about 0.5 mm in embodiments, and may be characterized by a thickness of less than or about 0.25 mm, less than or about 0.20 mm, less than or about 0.15 mm, less than or about 0.10 mm, less than or about 0.07 mm, less than or about 0.05 mm, less than or about 0.03 mm, less than or about 0.01 mm, or less. The ion-selective polymeric material may retain certain mechanical properties to allow application along manufacturing lines. For example, the ion-selective polymeric material may be characterized by a tensile or other strength in a machine direction of greater than or about 50 kg/cm$^2$ in embodiments, and may be characterized by a strength in a machine direction of greater than or about 100 kg/cm$^2$, greater than or about 150 kg/cm$^2$, greater than or about 200 kg/cm$^2$, greater than or about 250 kg/cm$^2$, greater than or about 300 kg/cm$^2$, greater than or about 350 kg/cm$^2$, greater than or about 400 kg/cm$^2$, greater than or about 450 kg/cm$^2$, greater than or about 500 kg/cm$^2$, greater than or about 550 kg/cm$^2$, greater than or about 600 kg/cm$^2$, greater than or about 650 kg/cm$^2$, greater than or about 700 kg/cm$^2$, greater than or about 750 kg/cm$^2$, or higher.

The ion-selective polymeric material may also be characterized by a diffusion ratio of different materials. For example, a diffusion ratio through the ion-selective polymeric material for water or hydroxide relative to metal ions, such as zinc or manganese, may be greater than 1. The diffusion ratio, such as permeability or diffusion of water or hydroxide as a ratio with the permeability or diffusion of metal ions, may be up to or greater than 10, up to or greater than 100, up to or greater than 1,000, up to or greater than 10,000, up to or greater than 100,000, up to or greater than 1,000,000, or higher, and may be up to 1:0 in which water or hydroxide may permeate the ion-selective polymeric material, but metal ions cannot pass through the ion-selective polymeric material.

For all materials within a cell structure, the ion-selective polymeric material may possess selectivities relative to each material. For example, the cationic backbone with anionic incorporation may provide an ion-selective polymeric material characterized by a selectivity for hydroxide ions or anions generally that is higher than the selectivity for zinc cations, manganese cations, or more generally metal cations. Additionally, the ion-selective polymeric materials under operation may produce metal-containing complexes, such as hydroxide complexes, and the selectivity may also extend to these or other metal-containing anions or metal-hydroxide complexes. Selectivity as used may be characterized both chemically and electrically. For example, the selectivity may be associated with ionic conductivity, which may relate to the movement of species across the polymeric material effected by an electric field. Additionally, the selectivity may be defined as a function of permeability and concentration of a particular component of the cell relative to all components of a cell.

The ion-selective polymeric materials may provide high ion selectivity, defined as a relatively high permeability of hydroxide ions based on a concentration of hydroxide ions, and a relatively low permeability of metal-hydroxide or other anionic metal-complexes cations based on a concentration of metal cations, such as zinc, manganese, iron, vanadium, and titanium, for example. Typically, this tradeoff affects water management within the cell as well, but the ion-selective polymeric materials may allow water diffusion through the polymeric materials, while limiting ionic transfer through the structure in one or more ways. For example, in some embodiments, permeability through the polymeric material may afford transportation of water and hydroxide ions, while limiting transmission of other ions. In other embodiments, the ion-selective polymeric material may limit or prevent both anion and cation transmission through the ion-selective polymeric material. The ion-selective polymeric material may be characterized with terminal groups or moieties including quarternary ammonium ions with associated hydroxide ions that may migrate towards one electrode or the other during charging or discharging operations.

The selectivity may additionally be related to pore and permeation path diameters across an ion-selective polymeric barrier. For example, the ion-selective polymeric material may be characterized by the capability of transporting ions of a certain size or diameter. It is to be understood that by diameter is meant a distance across a molecule or ion in any direction, as many materials may not be characterized by spherical geometries. The ion-selective polymeric material may be characterized by the capability of transporting materials characterized by a diameter of less than or about 50 nm, while limiting or preventing the transmission of materials characterized by a larger diameter. The ion-selective polymeric material may also be characterized by the capability of transporting materials characterized by a diameter of less than or about 45 nm, less than or about 40 nm, less than or about 35 nm, less than or about 30 nm, less than or about 25 nm, less than or about 20 nm, less than or about 15 nm, less than or about 10 nm, less than or about 9 nm, less than or about 8 nm, less than or about 7 nm, less than or about 6 nm, less than or about 5 nm, less than or about 4 nm, less than or about 3 nm, less than or about 2 nm, less than or about 1 nm, less than or about 0.5 nm, less than or about 0.3 nm, or less, while limiting or preventing transmission of materials characterized by a larger diameter.

The ion-selective polymeric materials may allow the separator 330 to be reduced in thickness or eliminated because of the ability of the ion-selective polymeric material to electrically insulate the positive and negative electrodes from each other. The separator 330 may be reduced in thickness compared to conventional separators, and in some embodiments may be removed from the system. For example, the separator 330 may be less than 0.25 mm in thickness, and may be less than or about 0.20 mm, less than or about 0.15 mm, less than or about 0.10 mm, less than or about 0.07 mm, less than or about 0.05 mm, less than or about 0.03 mm, less than or about 0.01 mm, or less.

Exemplary Prismatic Battery Cells

Figure 4:
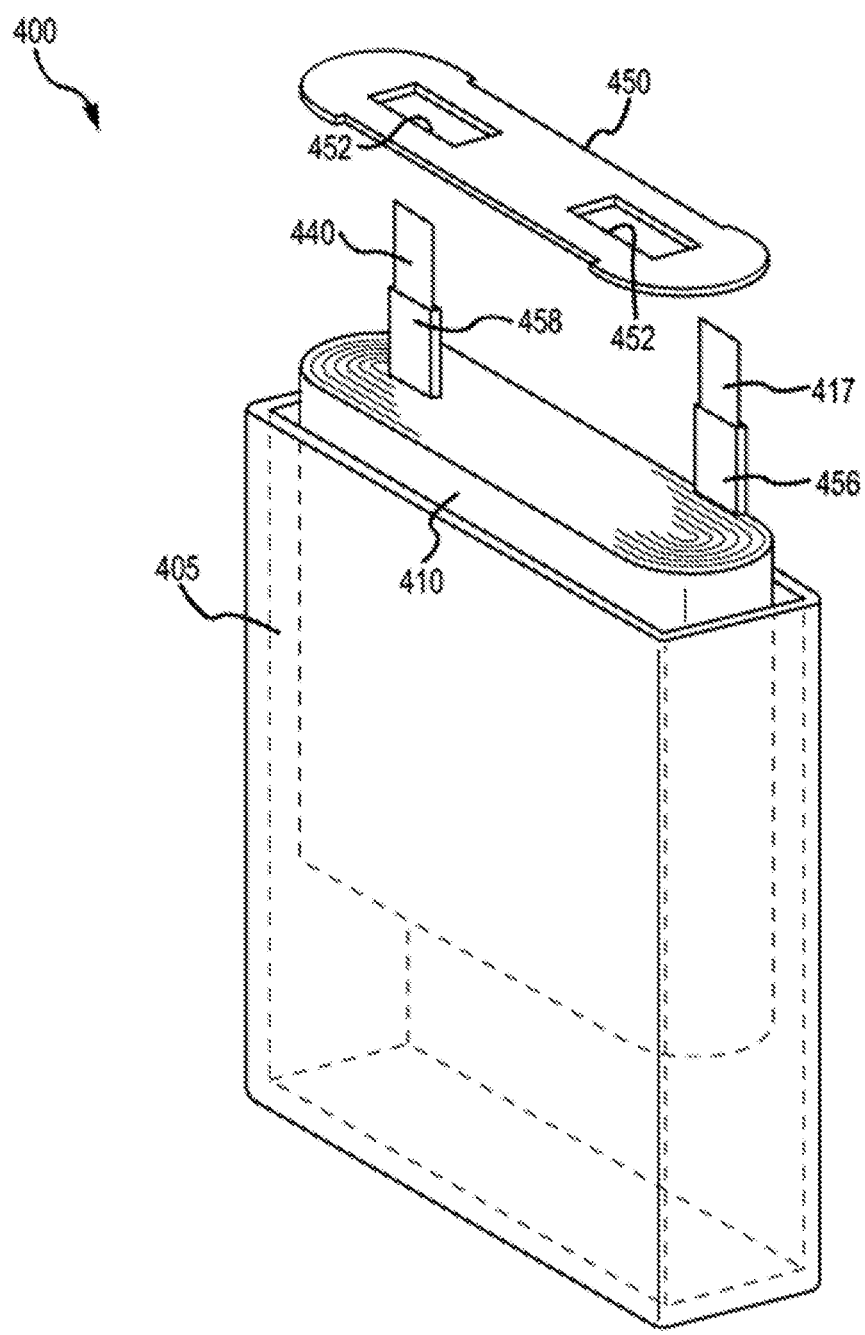
FIG. 4 shows a simplified schematic of a prismatic battery cell design that incorporates the present technology.

FIG. 4 shows a simplified schematic of a prismatic battery cell 400 that incorporates the present technology. Exemplary prismatic battery cell 400 may include an outer casing 405 that contains the components of the battery cell 400 including the electrolyte that acts as the transport medium for ion conduction between the positive and negative electrode materials. Within the outer casing 405 may be a rolled multilayer 410 that includes a positive electrode layer, an negative electrode layer, and a separator layer between the positive and negative electrode layers. The separator layer may be made from or incorporate ion-selective materials, polymers, and layers, such as those described for the plate type battery cells.

The positive electrode layer is attached to a positive current collector that includes (or is electrically coupled to) a positive terminal 417. The negative electrode layer is attached to a negative current collector that includes (or is electrically coupled to) a negative terminal 440. The prismatic battery cell 400 may also include a cover 450 that can be attached to the outer casing 405 to form an enclosure for the cell's internal components, including the rolled multilayer 410 and the electrolyte. The cover 450 may include openings 452 to permit the positive and negative terminals 417, 440 to extend beyond the outer casing 405 of the battery cell 400. In the embodiments shown, the positive and negative terminals 417, 440 are coated with sealing material 456, 458, to form a seal between the terminals 417, 440, and the openings 452. The seal may prevent liquid contents (e.g., electrolyte) from the interior of the prismatic battery cell 400 from leaking out of the cell.

Exemplary Pouch Battery Cells

Figure 5:
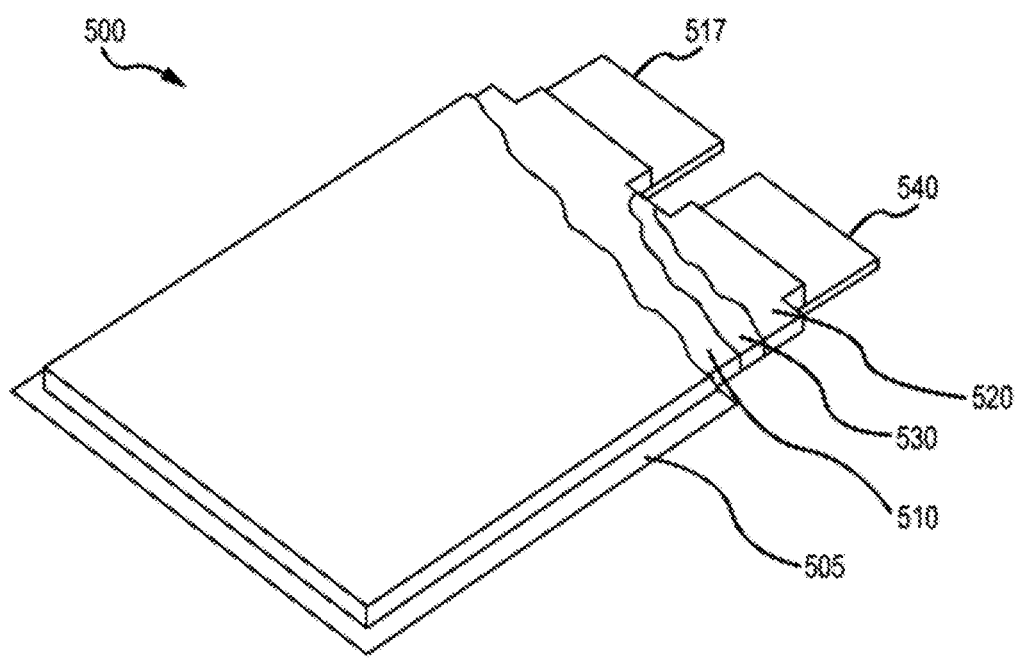
FIG. 5 shows a simplified schematic of a pouch battery cell design that incorporates the present technology.

FIG. 5 shows a simplified schematic of a pouch battery cell 500 that incorporates the present technology. Exemplary pouch battery cell 500 may include an outer casing 505 that contains the components of the battery cell 500. Within the outer casing 505 may be a positive pouch 510 that contains the positive electrode material and electrolyte, a negative electrode pouch 520 that contains the negative electrode material and electrolyte, and a separator 530 that permits ion conduction (e.g., $OH^-$ conduction) between the electrode materials in the positive pouch 510 and the negative electrode pouch 520. The positive pouch 510 may be electrically coupled to a positive current collector that includes (or is connected to) a positive terminal 517 of the pouch cell 500. The negative electrode pouch 520 may be electrically coupled to a negative current collector that includes (or is connected to) a negative terminal 540 of the pouch cell 500. The separator 530 may be made from or incorporate ion-selective materials, polymers, and layers, such as those described for the plate type battery cells.

Exemplary Cylindrical Battery Cells

Figure 6:
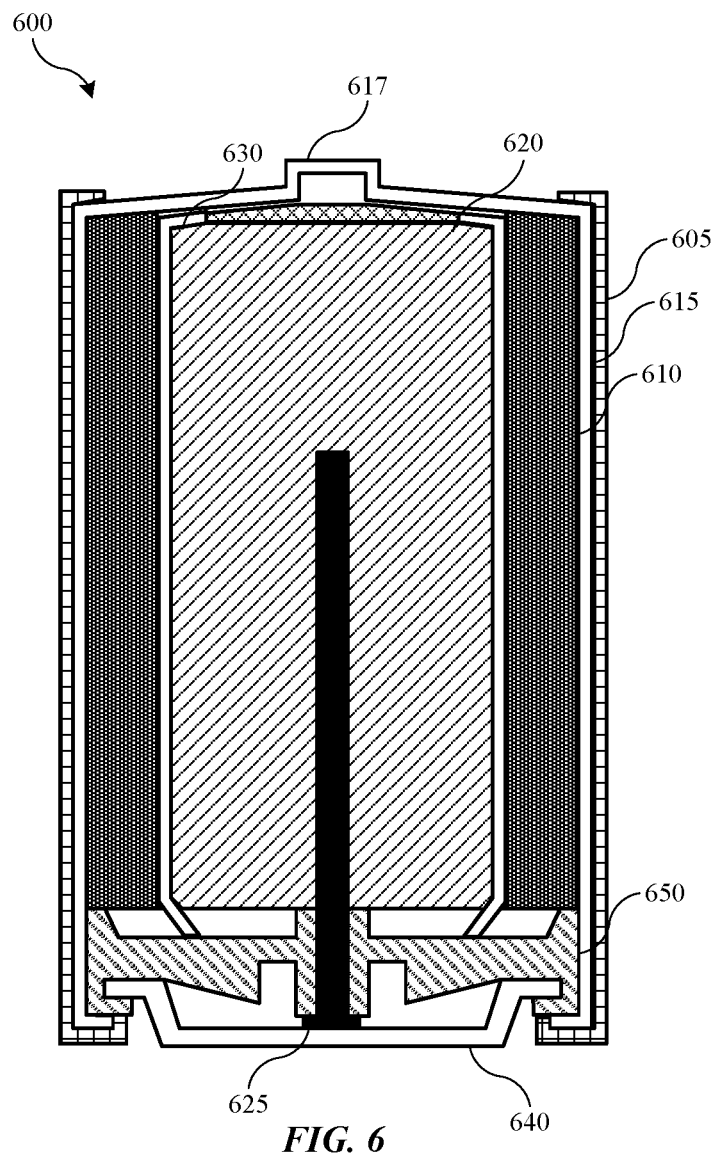
FIG. 6 shows a simplified schematic of a cylindrical battery cell design that incorporates the present technology.

FIG. 6 shows a simplified schematic of an exemplary cylindrical battery cell which can include the present technology. Exemplary cylindrical battery cell 600 may include an outer casing 605 that contains the components of the battery cell 600. Within outer casing 605 may be a positive active material 610, which may be in contact with a positive current collector 615. Positive current collector 615 may be coupled with an additional conductive element, or may form positive terminal 617 of the battery cell 600. Positive current collector 615 may be stainless steel, or some other conductive material suitable for electronic transmission. Battery cell 600 may also include a negative active material 620, which may be in contact with an negative current collector 625.

Negative current collector 625 may form or be coupled with an additional conductive element forming negative terminal 640. Negative current collector 625 may be brass, or some other conductive material suitable for electronic transmission. A separator 630 may be positioned between positive active material 610 and negative active material 620 to prevent short circuiting between the materials. A portion of separator 630 or a separate insulator may be positioned with the separator 630 to further limit contact of the negative active material 620 with the positive terminal 617. Additionally, an insulator 650 may be positioned between the negative current collector 625 and the positive active material 610 and the positive current collector 615. Insulator 650 may be composed of a flexible material to allow gas expansion within the cell during operation. The separator 630 may be made from or incorporate ion-selective materials, polymers, and layers, such as those described for the plate type battery cells.

Exemplary Button Battery Cells

Figure 7:
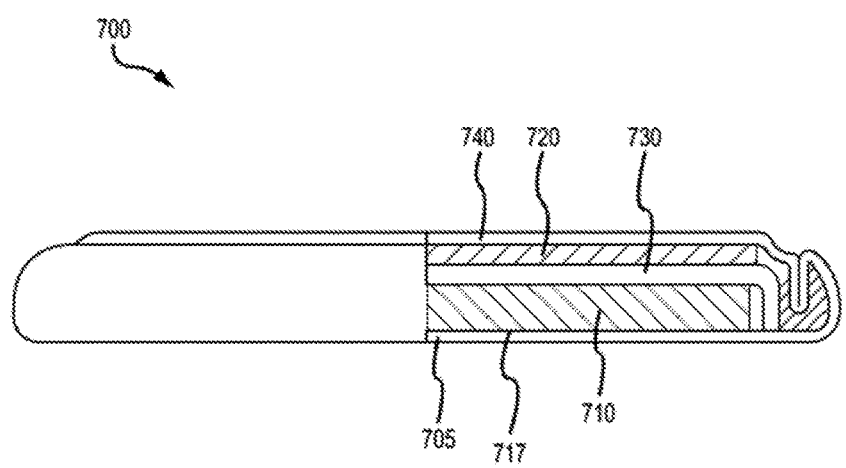
FIG. 7 shows a simplified schematic of a button battery cell design that incorporates the present technology.

FIG. 7 shows a simplified schematic of a button battery cell 700 that incorporates the present technology. Exemplary button battery cell 700 may include an outer can 705 that contains the positive electrode 710 and the negative electrode 720 of the battery cell. The outer can 705 also contains the separator 730 that permits ion conduction (e.g., $OH^-$ conduction) between the electrode materials in the positive electrode 710 and the negative electrode 720. The positive electrode 710 may be electrically coupled to a positive current collector that includes positive terminal 717 of the button cell 700. The negative electrode 720 may be electrically coupled to a negative electrode cap that includes a negative terminal 740 of the button cell 700. The separator 730 may be made from or incorporate ion-selective materials, polymers, and layers, such as those described for the plate type battery cells.

EXPERIMENTAL

Experiments were conducted to measure the effect of an redox mediator-containing electrolyte on the capacity and cycle life of battery cells that included a redox mediator-containing electrolyte. The experiments were conducted in a half-cell format in which the counter electrode was $Ni(OH)_2/NiOOH$ and the working electrode included manganese oxide ($MnO_2$). The electrodes were separated using an ion-selective membrane (a hydroxide conducting membrane) and the they maintain ionic conduct with an electrolyte that included water, aqueous 6M potassium hydroxide, and a redox mediator. The battery cells were tested at two different concentrations of the redox mediator in the electrolyte (0.1 wt. % or 1 wt. % of the total weight of the electrolyte). The battery cells were also tested with electrolytes either having (i) the redox mediator localized to contact with the positive electrode, or (ii) the redox mediator present throughout the electrolyte.

For each battery cell, the capacity of the $MnO_2$-containing working electrode material was measured (in mAh/g) in three ways: (1) oxidative capacity at a 0.5C charge rate after 6 charge/discharge cycles, (2) oxidative capacity at 0.5C after 87 charge/discharge cycles, and (3) reductive capacity averaged over 10 charge/discharge cycles from cycles 40 to 50. In addition the battery cells were measured for the number of charge/discharge cycles to reach 80% of initial capacity at 0.1C (i.e., C/10 cycle life). The type, concentration, and localization of the redox mediator the battery cells of Examples 1-35 are listed in Table 1 below:

TABLE 1

Redox Mediators in Alkaline Cells with $MnO_2$-Containing Working Electrode

| Example | Redox Mediator | Redox Med Conc (wt. %) | Redox Med Location |
|---|---|---|---|
| 1 (Comparative) | None | 0% | None |
| 2 | Sodium 1,2-Naphthoquinone-4-sulfonate | 1% | Pos Electrode |
| 3 | Sodium 1,2-Naphthoquinone-4-sulfonate | 1% | All Electrolyte |
| 4 | Sodium 1,2-Naphthoquinone-4-sulfonate | 0.1% | Pos Electrode |
| 5 | Sodium 1,2-Naphthoquinone-4-sulfonate | 0.1% | All Electrolyte |
| 6 | 1,8-dihydroxyanthraquinone | 1% | Pos Electrode |
| 7 | 1,8-dihydroxyanthraquinone | 1% | All Electrolyte |
| 8 | 1,8-dihydroxyanthraquinone | 0.1% | Pos Electrode |
| 9 | 1,8-dihydroxyanthraquinone | 0.1% | All Electrolyte |
| 10 | 3,4-dihydroxybenzaldehyde | 1% | Pos Electrode |
| 11 | 3,4-dihydroxybenzaldehyde | 1% | All Electrolyte |
| 12 | 3,4-dihydroxybenzaldehyde | 0.1% | Pos Electrode |
| 13 | 3-methylcatechol | 1% | Pos Electrode |
| 14 | 3-methylcatechol | 1% | All Electrolyte |
| 15 | 3-methylcatechol | 0.1% | Post Electrode |
| 16 | 3-methylcatechol | 0.1% | All Electrolyte |
| 17 | 4-carboxy TEMPO | 1% | Pos Electode |
| 18 | 4-carboxy TEMPO | 1% | All Electrolyte |
| 19 | 4-carboxy TEMPO | 0.1% | Pos Electrode |
| 20 | 4-carboxy TEMPO | 0.1% | All Electrolyte |
| 21 | 4-hydroxy TEMPO | 1% | Pos Electode |
| 22 | 4-hydroxy TEMPO | 0.1% | Pos Electode |
| 23 | 4-hydroxy TEMPO | 0.1% | All Electrolyte |
| 24 | 4-methylcatechol | 1% | Pos Electode |
| 25 | 4-methylcatechol | 0.1% | Pos Electode |
| 26 | 4-methylcatechol | 0.1% | All Electrolyte |
| 27 | 1,5-dihydroxyanthraquinone | 1% | Pos Electode |
| 28 | 1,5-dihydroxyanthraquinone | 1% | All Electrolyte |
| 29 | 1,3,8-trihydroxy-6-methyl-9,10-anthracenedione | 1% | Pos Electode |
| 30 | 1,3,8-trihydroxy-6-methyl-9,10-anthracenedione | 1% | All Electrolyte |
| 31 | 1,3,8-trihydroxy-6-methyl-9,10-anthracenedione | 0.1% | Pos Electode |
| 32 | 1,3,8-trihydroxy-6-methyl-9,10-anthracenedione | 0.1% | All Electrolyte |
| 33 | Potassium 2,5-dihydroxybenzene-sulfonate | 1% | All Electrolyte |
| 34 | Potassium 2,5-dihydroxybenzene-sulfonate | 0.1% | Pos Electrode |
| 35 | Potassium 2,5-dihydroxybenzene-sulfonate | 0.1% | All Electrolyte |

The battery cells of Examples 1-35 were tested for (1) oxidative capacity at a 0.5C charge rate after 6 charge/discharge cycles, (2) oxidative capacity at 0.5C after 87 charge/discharge cycles, (3) reductive capacity averaged over 10 charge/discharge cycles from cycles 40 to 50, and (4) the number of charge/discharge cycles to reach 80% of initial capacity at 0.1C (i.e., C/10 cycle life). All capacities were measured in milliamp hours per gram. Table 2 lists the performance of each battery cell based on the four performance characteristics:

TABLE 2

Battery Cell Performance with Redox Mediator-Containing Electrolytes

| Example | Cycle-6 Mn Ox 0.5C Capacity (mAh/g) | Cycle-87 Mn Ox 0.5C Capacity (mAh/g) | Avg Mn Red. Cycle Capacity for Cy 40-50 (mAh/g) | C/10 Cycle Life (#) |
|---|---|---|---|---|
| 1 (Comp) | 287.5 | 269.5 | 354.0 | 86 |
| 2 | 366.0 | 323.6 | 410.8 | 87 |
| 3 | 334.3 | 277.5 | 415.5 | 60 |
| 4 | 391.1 | 306.9 | 444.2 | 87 |
| 5 | 320.6 | 280.2 | 402.8 | 87 |
| 6 | 292.4 | 280.2 | 421.7 | 43.5 |
| 7 | 519.1 | 361.6 | 550.8 | 60 |
| 8 | 281.4 | 259.8 | 408.7 | 100.5 |
| 9 | 379.5 | 373.6 | 504.8 | 100.5 |
| 10 | 295.5 | 253.9 | 421.5 | 114 |
| 11 | 326.5 | 269.7 | 360.7 | 195 |
| 12 | 334.4 | 292.4 | 426.1 | 87 |
| 13 | 387.1 | 305.2 | 470.9 | 87 |
| 14 | 377.0 | 207.6 | 278.6 | 6 |
| 15 | 416.5 | 353.0 | 503.7 | 60 |
| 16 | 337.5 | 271.8 | 473.1 | 60 |
| 17 | 318.1 | 257.7 | 415.5 | 73.5 |
| 18 | 52.5 | 3.9 | 10.2 | 73.5 |
| 19 | 295.3 | 291.1 | 408.1 | 100.5 |
| 20 | 344.3 | 298.4 | 466.4 | 138 |
| 21 | 270.5 | 274.0 | 355.2 | 87 |
| 22 | 357.7 | 302.4 | 402.6 | 114 |
| 23 | 340.8 | 262.0 | 482.1 | 87 |
| 24 | 366.3 | 283.3 | 533.3 | 33 |
| 25 | 339.5 | 323.8 | 446.3 | 100.5 |
| 26 | 379.8 | 261.2 | 450.2 | 60 |
| 27 | 306.9 | 278.4 | 454.6 | 114 |
| 28 | 383.1 | 343.9 | 498.5 | |
| 29 | 260.9 | 239.0 | 372.7 | 100.5 |
| 30 | 360.6 | 317.2 | 397.2 | 87 |
| 31 | 374.5 | 277.4 | 397.9 | 73.5 |
| 32 | 444.5 | 344.6 | 473.8 | 73.5 |
| 33 | 435.6 | 316.5 | 452.4 | 46.5 |
| 34 | 387.7 | 249.1 | 474.8 | 60 |
| 35 | 369.0 | 255.0 | 469.0 | 73.5 |

The test results improvements in several of the battery cells compared to Comparative Example 1 where no redox mediator was included in the electrolyte. For example, the redox mediator 3-methylcatechol increased the Cy-6 oxidative capacity of the battery cell in Example 13 to approximately 390 mAh/g compared to approximately 290 mAh/g for Comparative Example 1. Table 2 also shows redox mediator 3,4-dihydroxybenzaldehyde increased the cycle life of the battery cell in Example 10 to 114 cycles compared to approximately 86 cycles for Comparative Example 1. Table 2 further shows that redox mediator 4-carboxy TEMPO increased the Cy-6 oxidative capacity of the battery cell in Example 20 to approximately 345 mAh/g and cycle life to 138 cycles compared to 290 mAh/g and 86 cycles, respectively, for Comparative Example 1.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having disclosed several embodiments, it will be recognized by those of skill in the art that various modifications, alternative constructions, and equivalents may be used without departing from the spirit of the embodiments. Additionally, a number of well-known processes and elements have not been described in order to avoid unnecessarily obscuring the present technology. Accordingly, the above description should not be taken as limiting the scope of the technology.

Where a range of values is provided, it is understood that each intervening value, to the smallest fraction of the unit of the lower limit, unless the context clearly dictates otherwise, between the upper and lower limits of that range is also specifically disclosed. Any narrower range between any stated values or unstated intervening values in a stated range and any other stated or intervening value in that stated range is encompassed. The upper and lower limits of those smaller ranges may independently be included or excluded in the range, and each range where either, neither, or both limits are included in the smaller ranges is also encompassed within the technology, subject to any specifically excluded limit in the stated range. Where the stated range includes one or both of the limits, ranges excluding either or both of those included limits are also included. Where multiple values are provided in a list, any range encompassing or based on any of those values is similarly specifically disclosed.

As used herein and in the appended claims, the singular forms "a", "an", and "the" include plural references unless the context clearly dictates otherwise. Thus, for example, reference to "a material" includes a plurality of such materials, and reference to "the cell" includes reference to one or more cells and equivalents thereof known to those skilled in the art, and so forth.

Also, the words "comprise(s)", "comprising", "contain(s)", "containing", "include(s)", and "including", when used in this specification and in the following claims, are intended to specify the presence of stated features, integers, components, or operations, but they do not preclude the presence or addition of one or more other features, integers, components, operations, acts, or groups.

What is claimed is:

1. A redox mediator-containing electrolyte incorporated in a battery cell, wherein the redox mediator-containing electrolyte comprises:
    water;
    at least one hydroxide salt dissolved in the water; and
    at least one redox mediator incorporated into the water, wherein the at least one redox mediator increases at least one of a rate capability or a cycle life of the battery cell by at least 10%, and
    wherein the battery cell is an alkaline battery cell selected from the group consisting of a prismatic battery cell, a pouch battery cell, a cylindrical battery cell, and a button battery cell.

2. The redox mediator-containing electrolyte of claim 1, wherein the at least one hydroxide salt comprises sodium hydroxide, potassium hydroxide, ammonium hydroxide, or alkylammonium hydroxide.

3. The redox mediator-containing electrolyte of claim 1, wherein the at least one redox mediator mediates a redox reaction of a manganese-containing compound.

4. The redox mediator-containing electrolyte of claim 3, wherein the manganese-containing compound is $MnO_2$.

5. The redox mediator-containing electrolyte of claim 3, wherein the at least one redox mediator has a charging oxidation/reduction potential ranging from −0.2V to 0.3V versus a standard hydrogen electrode for manganese charging.

6. The redox mediator-containing electrolyte of claim 3, wherein the at least one redox mediator has a discharging oxidation/reduction potential ranging from −0.2V to −0.8V versus a standard hydrogen electrode for manganese discharging.

7. The redox mediator-containing electrolyte of claim 1, wherein the redox mediator comprises at least one of a quinone compound, a 2,2,6,6-tetramethylpiperidin 1-oxyl (TEMPO) compound, a triphenyl amine compound, a tetrathiafulvalene compound, a tetracyanoquinodimethane compound, a metal-oxolate compound, a metal-polyazamacrocycle compound, a metal-polyamine compound, a metal-polypyridyl compound, a metal-tertiary amine compound, a metal-porphyrin compound, or a metal-salen compound.

8. The redox mediator-containing electrolyte of claim 1, wherein the at least one redox mediator comprises at least one of 3-methylcatecol, 3,4-dihydroxybenzaldehyde, or 4-carboxy-TEMPO.

9. The redox mediator-containing electrolyte of claim 1, wherein the redox mediator comprises at least one of a pyridine compound, a tacn compound, a cyclen compound, a cyclam compound, a porphyrin compound, or a salen compound.

10. The redox mediator-containing electrolyte of claim 1, wherein the redox mediator comprises a polycarboxylic acid.

11. The redox mediator-containing electrolyte of claim 1, wherein the redox mediator comprises a polyamine compound.

12. The redox mediator-containing electrolyte of claim 1, wherein the redox mediator comprises a pyridine compound, a quinoline compound, an isoquinoline compound, an anthraquinone compound, or a triphenyl compound.

13. The redox mediator-containing electrolyte of claim 1, wherein the redox mediator-containing electrolyte has a pH ranging from about 13 to about 15.

14. The redox mediator-containing electrolyte of claim 1, wherein the redox mediator-containing electrolyte has a hydroxide ion concentration ranging from about 6M to about 15M.

15. The redox mediator-containing electrolyte of claim 1, wherein the redox mediator-containing electrolyte has a hydroxide ion concentration ranging from about 9M to about 12M.

16. The redox mediator-containing electrolyte of claim 1, wherein the battery cell further comprises an ion-selective material.

17. The redox mediator-containing electrolyte of claim 16, wherein the ion-selective material diffuses hydroxide ions through the material at a faster rate than at least one of the redox mediators.

18. The redox mediator-containing electrolyte of claim 16, wherein at least one of the redox mediators is in contact with a positive electrode of the battery cell and isolated from a negative electrode of the battery cell by the ion-selective material.

19. The redox mediator-containing electrolyte of claim 16, wherein at least one of the redox mediators is in contact with a negative electrode of the battery cell and isolated from a positive electrode of the battery cell by the ion-selective material.

20. A battery cell comprising:
    a positive electrode;
    a negative electrode; and
    an redox mediator-containing electrolyte, wherein the redox mediator-containing electrolyte comprises:
    water;
    at least one hydroxide salt dissolved in the water; and
    at least one redox mediator incorporated into the water, wherein the at least one redox mediator increases at least one of a rate capability or a cycle life of the battery cell by at least 10%, and wherein the battery cell is an alkaline battery cell selected from the group consisting of a prismatic battery cell, a pouch battery cell, a cylindrical battery cell, and a button battery cell.

21. The battery cell of claim 20, wherein the battery cell further comprises an ion-selective barrier between the positive electrode and the negative electrode, wherein the ion selective barrier has a diffusion ratio of hydroxide ions to at least one of the redox mediators of at least 10:1.

22. The battery cell of claim 20, wherein at least one of the redox mediators is in contact with the positive electrode and isolated from the negative electrode of by the ion-selective barrier.

23. The battery cell of claim 20, wherein at least one of the redox mediators is in contact with the negative electrode and isolated from the positive electrode of by the ion-selective barrier.

24. The battery cell of claim 20, wherein the ion-selective barrier forms an electrically insulating separator between the positive electrode and the negative electrode.

25. The battery cell of claim 20, wherein the ion-selective barrier coats an outer surface of at least one of the positive electrode or the negative electrode.

26. The battery cell of claim 20, wherein the ion-selective barrier is incorporated into at least one of the positive electrode or the negative electrode.

27. The battery cell of claim 20, wherein the positive electrode comprises at least one manganese-containing compound.

\* \* \* \* \*